(12) United States Patent
Behnam et al.

(10) Patent No.: US 11,123,018 B2
(45) Date of Patent: Sep. 21, 2021

(54) EXTRACTING A MOTHER WAVELET FUNCTION FOR DETECTING EPILLEPTIC SEIZURE

(71) Applicants: Morteza Behnam, Najafabad (IR); Hossein Pourghassem, Najafabad (IR)

(72) Inventors: Morteza Behnam, Najafabad (IR); Hossein Pourghassem, Najafabad (IR)

(73) Assignees: ISLAMIC AZAD UNIVERSITY, NAJAFABAD BRANCH, Najafabad (IR); Morteza Behnam, Isfahan (IR); Hossein Pourghassem, Isfahan (IR)

( * ) Notice: Subject to any disclaimer, the term of this patent is extended or adjusted under 35 U.S.C. 154(b) by 616 days.

(21) Appl. No.: 15/992,161

(22) Filed: May 29, 2018

(65) Prior Publication Data
US 2019/0000390 A1    Jan. 3, 2019

Related U.S. Application Data

(60) Provisional application No. 62/512,014, filed on May 28, 2017.

(51) Int. Cl.
| | |
|---|---|
| *A61B 5/00* | (2006.01) |
| *G06F 17/14* | (2006.01) |
| *G06K 9/46* | (2006.01) |
| *G16H 50/20* | (2018.01) |
| *G06K 9/00* | (2006.01) |

(Continued)

(52) U.S. Cl.
CPC ............... *A61B 5/726* (2013.01); *A61B 5/30* (2021.01); *A61B 5/316* (2021.01); *A61B 5/374* (2021.01); *A61B 5/4094* (2013.01); *A61B 5/7264* (2013.01); *G06F 17/148* (2013.01); *G06K 9/0053* (2013.01); *G06K 9/0055* (2013.01); *G06K 9/00516* (2013.01); *G06K 9/00523* (2013.01); *G06K 9/00536* (2013.01); *G06K 9/4619* (2013.01); *G16H 50/30* (2018.01); *G16H 50/70* (2018.01); *A61B 5/7267* (2013.01); *G16H 50/20* (2018.01)

(58) Field of Classification Search
CPC combination set(s) only.
See application file for complete search history.

(56) References Cited

U.S. PATENT DOCUMENTS

| | | | |
|---|---|---|---|
| 5,345,934 A * | 9/1994 | Highe | ............... A61B 5/0017 600/372 |
| 6,658,287 B1 | 12/2003 | Litt et al. | |

(Continued)

FOREIGN PATENT DOCUMENTS

CN          104887224         4/2018

OTHER PUBLICATIONS

Gandhi, T., et al. "Expert Model for Detection of Epileptic Activity in EEG Signature" Expert Systems with Applications, vol. 37, pp. 3513-3520 (2010) (Year: 2010).*

(Continued)

*Primary Examiner* — Jay Hann
(74) *Attorney, Agent, or Firm* — Bajwa IP Law Firm; Haris Zaheer Bajwa

(57) ABSTRACT

A method for creating a mother wavelet function. The method includes preparing a plurality of vectors, extracting a kernel from the plurality of vectors, and extracting the mother wavelet function from the kernel. The kernel includes a mode value of a vector of the plurality of vectors.

14 Claims, 29 Drawing Sheets

(51) Int. Cl.
*G16H 50/70* (2018.01)
*A61B 5/30* (2021.01)
*A61B 5/316* (2021.01)
*A61B 5/374* (2021.01)
*G16H 50/30* (2018.01)

(56) References Cited

U.S. PATENT DOCUMENTS

| | | | | |
|---|---|---|---|---|
| 7,299,088 | B1* | 11/2007 | Thakor | A61B 5/048 600/544 |
| 7,376,688 | B1* | 5/2008 | von der Embse | G06F 17/148 708/300 |
| 7,603,238 | B2* | 10/2009 | Valero | G01V 1/30 367/73 |
| 7,942,824 | B1* | 5/2011 | Kayyali | A61M 16/0051 600/538 |
| 9,737,230 | B2 | 8/2017 | Sarma et al. | |
| 10,426,365 | B1* | 10/2019 | Parhi | A61B 5/7275 |
| 10,531,806 | B2* | 1/2020 | Principe | A61B 5/16 |
| 2002/0035338 | A1 | 3/2002 | Dear et al. | |
| 2009/0082689 | A1 | 3/2009 | Guttag et al. | |
| 2011/0257517 | A1 | 10/2011 | Guttag et al. | |
| 2014/0358025 | A1 | 12/2014 | Parhi et al. | |
| 2015/0164377 | A1* | 6/2015 | Nathan | A61B 5/6802 600/595 |
| 2016/0029946 | A1* | 2/2016 | Simon | A61B 5/048 600/544 |
| 2017/0231519 | A1* | 8/2017 | Westover | A61B 5/0476 600/544 |
| 2017/0258390 | A1* | 9/2017 | Howard | A61B 5/4803 |

OTHER PUBLICATIONS

Panda, R., et al. "Classification of EEG Signal Using Wavelet Transform and Support Vector Machine for Epileptic Seizure Diction" IEEE Proceedings of 2010 Int'l Conf. on Systems in Medicine & Biology (2010) (Year: 2010).*

Nasehi, S. & Pourghassem, H. "Automatic Prediction of Epileptic Seizure Using Kernel Fisher Discriminant Classifiers" IEEE Int'l Conf. on Intelligent Computation & Bio-Medical Instrumentation (2011) (Year: 2011).*

Nasehi, S. & Pourghassem, H. "A Novel Effective Feature Selection Algorithm based on S-PCA and Wavelet Transform Features in EEG Signal Classification" IEEE 3rd Int'l Conf. on Communication Software & Networks (2011) available from <https://ieeexplore.ieee.org/abstract/document/6014686> (Year: 2011).*

Khan, Y., et al. "Automated Seizure Detection in Scalp EEG Using Multiple Wavelet Scales" IEEE Int'l Conf. on Signal Processing, Computing & Control (2012) available from <https://ieeexplore.ieee.org/abstract/document/6224361> (Year: 2012).*

Al-Qazzaz, N., et al. "Selection of Mother Wavelet Functions for Multi-Channel EEG Signal Analysis during a Working Memory Task" Sensors, vol. 15, p. 29015-29035 (2015) (Year: 2015).*

Harpale, V. & Bairagi, V. "Time and Frequency Domain Analysis of EEG Signals for Seizure Detection: A Review" IEEE Int'l Conf. on Microelectronics, Computing & Communications (2016) available from <https://ieeexplore.ieee.org/document/7522581> (Year: 2016).*

Vidyaratne, L. & Iftekharuddin, K. "Real-Time Epileptic Seizure Detection Using EEG" IEEE Transactions on Neural Systems & Rehabilitation Engineering, vol. 25, No. 11 (2017) (Year: 2017).*

Fathima, T., et al. "Wavelet Based Features for Epileptic Seizure Detection" MES J. of Tech. & Management, vol. 2, No. 1, p. 108-112 (2011) (Year: 2011).*

Husain, S. & Rao, K. "An Artificial Neural Network Model for Classification of Epileptic Seizures Using Huang-Hilbert Transform" Int'l J. on Soft Computing, vol. 5, No. 3, pp. 23-33 (2014) (Year: 2014).*

Behnam, M. & Pourghassem, H. "Real-Time Seizure Prediction Using RLS Filtering and Interpolated Histogram Feature Based on Hybrid Optimization Algorithm of Bayesian Classifier and Hunting Search" Computer Methods & Programs in Biomedicine, vol. 132, pp. 115-136 (Apr. 2016) (Year: 2016).*

Behnam, M. & Pourghassem, H. "Periodogram Pattern Feature-based Seizure Detection Algorithm using Optimized Hybrid Model of MLP and Ant Colony" IEEE 23rd Iranian Conf. on Electrical Engineering, pp. 32-37 (2015) (Year: 2015).*

Orosco et al. "Patient non-specific algorithm for seizures detection in scalp EEG." Computers in biology and medicine 71 (2016): 128-134.

Bhatia et al. "Epilepsy Seizure Detection Using Wavelet Support Vector Machine Classifier." International Journal of Bio-Science and Bio-Technology 8, No. 2 (2016): 11-22.

Faust et al. "Wavelet-based EEG processing for computer-aided seizure detection and epilepsy diagnosis." Seizure—European Journal of Epilepsy 26 (2015): 56-64.

D'Alessandro et al. "A genetic approach to selecting the optimal feature for epileptic seizure prediction." In Engineering in Medicine and Biology Society, 2001. Proceedings of the 23rd Annual International Conference of the IEEE, vol. 2, pp. 1703-1706. IEEE, 2001.

Islam et al. "A wavelet-based artifact reduction from scalp EEG for epileptic seizure detection." IEEE journal of biomedical and health informatics20, No. 5 (2016): 1321-1332.

D'Alessandro et al. "Epileptic seizure prediction using hybrid feature selection over multiple intracranial EEG electrode contacts: a report of four patients." IEEE Transactions on Biomedical Engineering50, No. 5 (2003): 603-615.

Zandi et al. "Automated real-time epileptic seizure detection in scalp EEG recordings using an algorithm based on wavelet packet transform." IEEE Transactions on Biomedical Engineering 57, No. 7 (2010): 1639-1651.

Gajic et al. "Classification of EEG signals for detection of epileptic seizures based on wavelets and statistical pattern recognition." Biomedical Engineering: Applications, Basis and Communications 26, No. 02 (2014): 1450021.

Ayinala et al. "Low complexity algorithm for seizure prediction using Adaboost." In Engineering in Medicine and Biology Society (EMBC), 2012 Annual International Conference of the IEEE, pp. 1061-1064. IEEE, 2012.

Bandarabadi et al. "Seizure prediction with bipolar spectral power features using Adaboost and SVM classifiers." In Engineering in Medicine and Biology Society (EMBC), 2013 35th Annual International Conference of the IEEE, pp. 6305-6308. IEEE, 2013.

Ge et al. "A boosted cascade for efficient epileptic seizure detection." In Engineering in Medicine and Biology Society (EMBC), 2013 35th Annual International Conference of the IEEE, pp. 6309-6312. IEEE, 2013.

Liu et al. "Model-based spike detection of epileptic EEG data." Sensors 13, No. 9 (2013): 12536-12547.

Behnam et al. "Seizure-specific wavelet (Seizlet) design for epileptic seizure detection using CorrEntropy ellipse features based on seizure modulus maximas patterns." Journal of neuroscience methods 276 (2017): 84-107.

* cited by examiner

EXTRACTING A MOTHER WAVELET FUNCTION FOR DETECTING EPILEPTIC SEIZURE

CROSS-REFERENCE TO RELATED APPLICATION

This application claims the benefit of priority from U.S. Provisional Patent Application Ser. No. 62/512,014, filed on May 28, 2017, and entitled "METHOD AND INTELLIGENT SOFTWARE SYSTEM FOR EPILEPTIC SEIZURE DETECTION USING SEIZLET DESIGN," which is incorporated herein by reference in its entirety.

TECHNICAL FIELD

The present disclosure generally relates to electrical signal processing, and particularly, to electroencephalography (EEG) signal processing for seizure detection.

BACKGROUND

Epileptic seizure is as a disorder of central nervous system (CNS) due to electrical-ionic activities of nerve cells by discharging and leaking out intra-cellular fluids to other lobes and parts of the brain. After this diffusion event, electrical orders and undesirable impulses are frequently sent towards subjects' organs under the command of sympathetic and parasympathetic nervous systems and they reveal temporal and transient behaviors. These phenomena can be revealed by a state such as drowsiness or a temporary paralysis.

Electroencephalography (EEG) signals may be used for detecting and analyzing epileptic seizures. Existing issues of seizure detection by processing EEG signals may include obtaining acceptable detection measures, including accuracy, precision, sensitivity and specificity, and properly utilizing samples of the EEG signals (including short-term and long-term signals), and EEG channels, and specifying algorithms for different patients and different types of seizures.

A number of features may be extracted from EEG signals for seizure detection. The features may include time domain features, frequency domain features, and time-frequency domain features. The time domain features may have low accuracy for seizure detection. The frequency domain features may be more appropriate for analyzing stationary signals. Although short time epochs of EEG signals may be considered wide sense stationary processes, dynamics of EEG signals, such as sudden shifts from normal brain rhythms and activities to irregular frequency comportment variations may raise limitations in specifying the dynamics of seizure signals, and consequently, in the distinction between seizure and non-seizure behaviors.

Wavelet transforms are a type of time-frequency transforms that can be used for analyzing EEG signals. The wavelet transforms may be more suitable than time and frequency transforms for analyzing non-stationary time series such as EEG signals. However, due to a random nature of seizure attacks and also capturing multi-channel EEG signals, characteristics of seizure signals in different channels may include dissimilar comportments. Furthermore, extracted features based on coefficients of the time-frequency domain of EEG signals may be confused with other phenomena, including bruxism, sleep spindle, narcolepsy and states of sleep, due to the frequency bandwidth of EEG signals. Therefore, the coefficient-based features that are extracted whether by using power and energy distributions or based on the variations of time-frequency components may lack robust attributes for describing epileptic seizure attacks.

There is, therefore, a need for an exclusive wavelet kernel that is obtained according to the dynamics of EEG signals of patients with a history of epileptic seizure for appropriately extracting seizure patterns. There is also a need for a method for extracting suitable patterns of EEG signals of patients with a history of epileptic seizure as a basis of feature extraction for epileptic seizure detection and prediction.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes a method for creating a mother wavelet function. The method includes preparing a plurality of vectors, extracting a kernel from the plurality of vectors, and extracting the mother wavelet function from the kernel. In other implementations, the kernel may include a mode value of a vector of the plurality of vectors.

The above general aspect may include one or more of the following features. In an implementations, preparing the plurality of vectors may include preparing a plurality of signals, extracting a plurality of epochs from the plurality of signals, and extracting the plurality of vectors from the plurality of epochs. The plurality of signals may include a plurality of samples In another implementation, the plurality of epochs may include a first epoch and a second epoch. Each of the plurality of epochs may include a given number of samples of the plurality of samples. In an example, each vector of the plurality of vectors may include a first sample of the first epoch and a second sample of the second epoch.

In some implementations, preparing the plurality of signals may include acquiring a plurality of electroencephalography (EEG) signals via a plurality of EEG channels, band-pass filtering each of the plurality of EEG signals based on a Kaiser-Bessel windowing procedure, and synchronizing the plurality of EEG signals by an event-based approach.

In some cases, extracting the kernel may include estimating a multimodal ensemble probability density function (PDF) for the vector by using an expectation maximization (EM) technique for a Gaussian mixture model (GMM) of the vector, and choosing a sample of the vector with a maximum value in the multimodal ensemble PDF as the mode value of the vector.

In different implementations, extracting the mother wavelet function may include fitting a polynomial function to the kernel, generating a wavelet scaling function from the polynomial function, and generating the mother wavelet function from the scaling function.

In an example, fitting the polynomial function to the kernel may include generating a resampled kernel by resampling the kernel with a given resampling rate, generating a local maximum array, and fitting a Lagrange polynomial function to the local maximum array. In another example, the local maximum array may include a plurality of local maximum values of the resampled kernel.

In some implementations, generating the mother wavelet function may include generating a low-pass filter from the wavelet scaling function, generating a high-pass filter from the low-pass filter, and generating the mother wavelet function from the low-pass filter.

Other systems, methods, features and advantages of the implementations will be, or will become, apparent to one of ordinary skill in the art upon examination of the following figures and detailed description. It is intended that all such additional systems, methods, features and advantages be included within this description and this summary, be within the scope of the implementations, and be protected by the claims herein.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Herein is disclosed a novel method and system for epileptic seizure detection and prediction. The method acquires EEG signals from a predefined set of channels, and classifies the signals in a seizure class and a non-seizure classes. For this purpose, a number of patterns of EEG signal variations may be extracted from the signals. Based on the patterns, a similarity measure may be defined to extract a set of features assessing the similarity of different segments of the EEG signal. The EEG signal is then classified based on the feature value, in the seizure or the non-seizure class by using a number of cascaded classifiers.

To extract the patterns of EEG signal variations, a wavelet transform is calculated for the EEG signals, and a cone of influence (COI) map is obtained for the wavelet transform. The patterns may be then extracted from the COI map. The wavelet transform is based on a mother wavelet function that is extracted from the EEG signals. To obtain the mother wavelet function, the EEG signals may be divided into a number of epochs, and a kernel may be extracted from the epochs that includes amplitude-based values with maximum repetition in the epochs at each time instant. A wavelet scaling function is then obtained from the kernel, and the mother wavelet function is generated according to kernel.

Figure 1A:
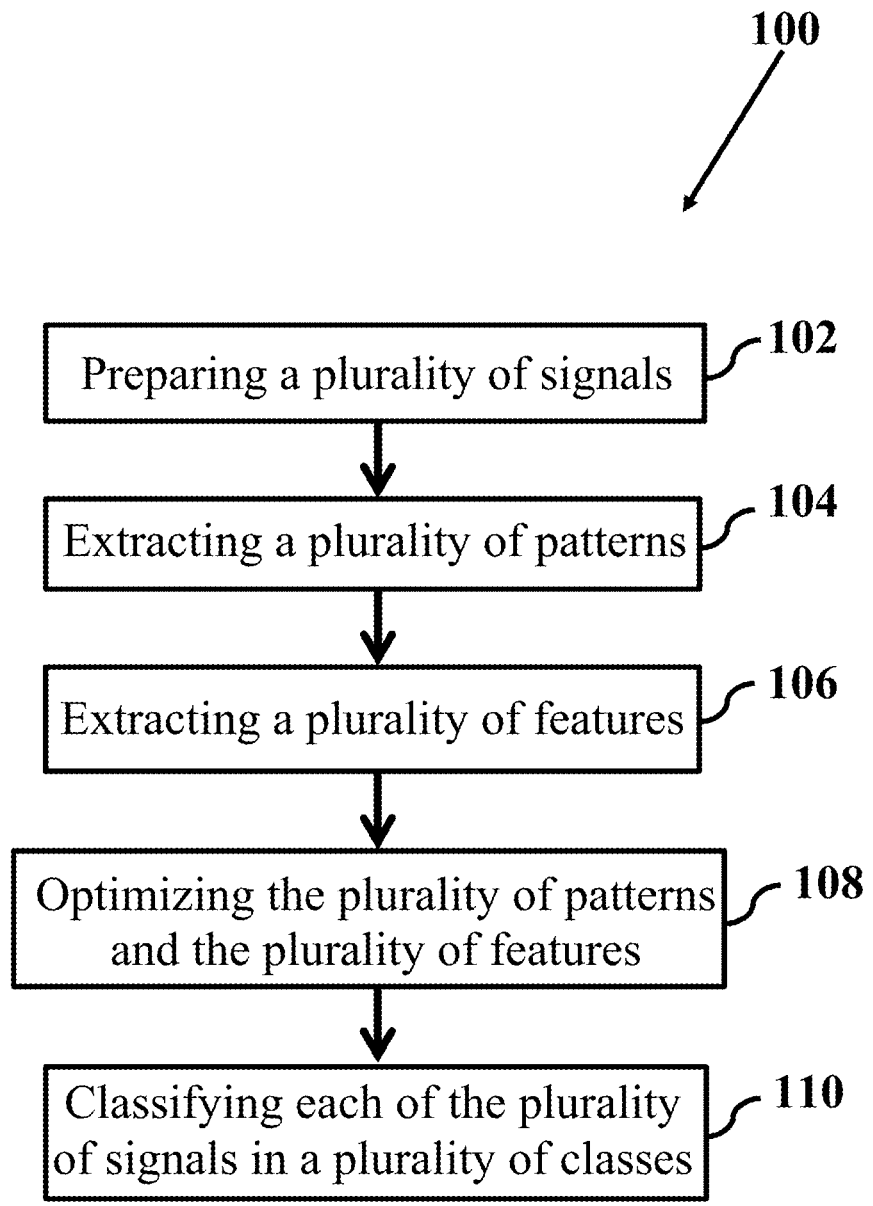
FIG. 1A is a flowchart of an implementation of a method for detecting and predicting an epileptic seizure according to one implementation of the present disclosure.

FIG. 1A is a flowchart of an implementation of a method 100 for detecting and predicting an epileptic seizure. In some implementations, the method 100 may include preparing a plurality of signals (a first step 102), extracting a plurality of patterns from the plurality of signals (a second step 104), extracting a plurality of features from the plurality of signals by applying the plurality of patterns on the plurality of signals (a third step 106), optimizing the plurality of patterns and the plurality of features (a fourth step 108), and classifying each of the plurality of signals in a plurality of classes by applying a plurality of classifiers on the plurality of features (a fifth step 110). In some examples, the plurality of classes may include a seizure class and a non-seizure class, and the plurality of classifiers may include a plurality of cascaded AdaBoost classifiers. The plurality of signals may include a plurality of samples.

In different implementations, preparing the plurality of signals (the first step 102) may include acquiring a plurality of electroencephalography (EEG) signals via a plurality of EEG channels, band-pass filtering each of the plurality of EEG signals based on a Kaiser-Bessel windowing procedure, and synchronizing the plurality of EEG signals by an event-based approach. In an implementation, the cutoff frequencies of a band-pass filter may be tuned on 0.5 up to 35 Hz. In another implementation, the authorized ripples may be about 0.01 in the pass band and may be about 0.05 in the stop band.

Figure 1B:
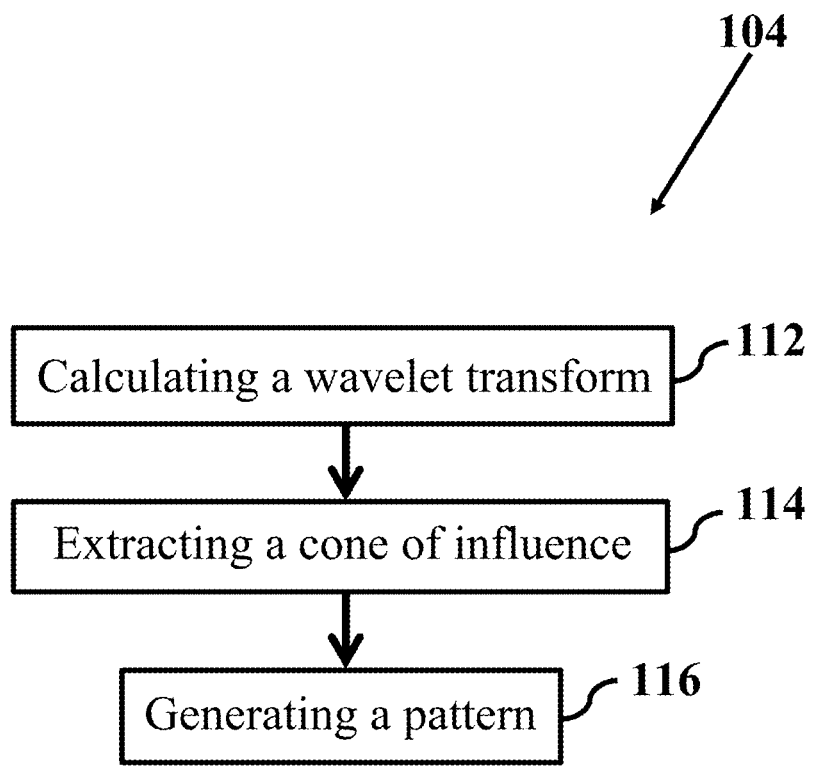
FIG. 1B is a flowchart of an implementation of extracting a plurality of patterns from a plurality of signals according to one implementation of the present disclosure.

FIG. 1B is a flowchart of an implementation of the second step 104. In some implementations, extracting the plurality of patterns (the second step 104) may include calculating a wavelet transform of a signal of the plurality of signals (a first step 112), extracting a cone of influence (COI) of the wavelet transform (a second step 114), and generating a pattern of the plurality of patterns according to the COI (a third step 116). In an implementation, calculating a wavelet transform of a signal of the plurality of signals (the first step 112) may include generating a mother wavelet function, and applying the mother wavelet function on the signal.

Figure 1C:
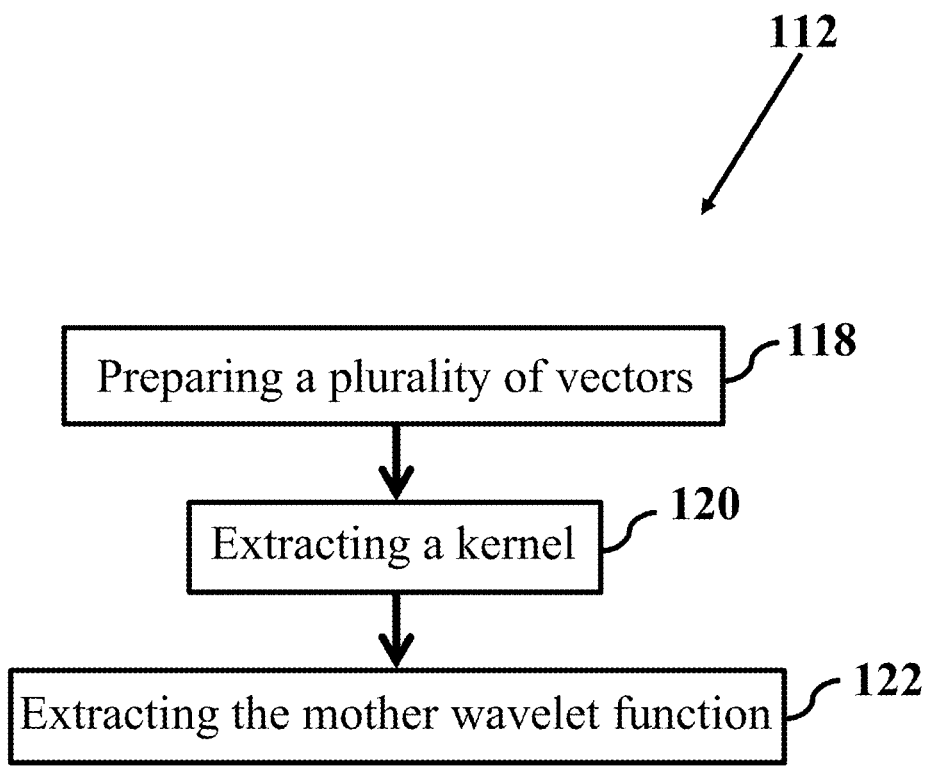
FIG. 1C is a flowchart of an implementation of calculating a wavelet transform of a signal according to one implementation of the present disclosure.

FIG. 1C is a flowchart of an implementation of the first step 112. In some implementations, calculating the wavelet transform (the first step 112) may include preparing a plurality of vectors (a first step 118), extracting a kernel from the plurality of vectors (a second step 120), and extracting the mother wavelet function from the kernel (a third step 122). In an example, the kernel may include a mode value of a vector of the plurality of vectors.

Figure 2:
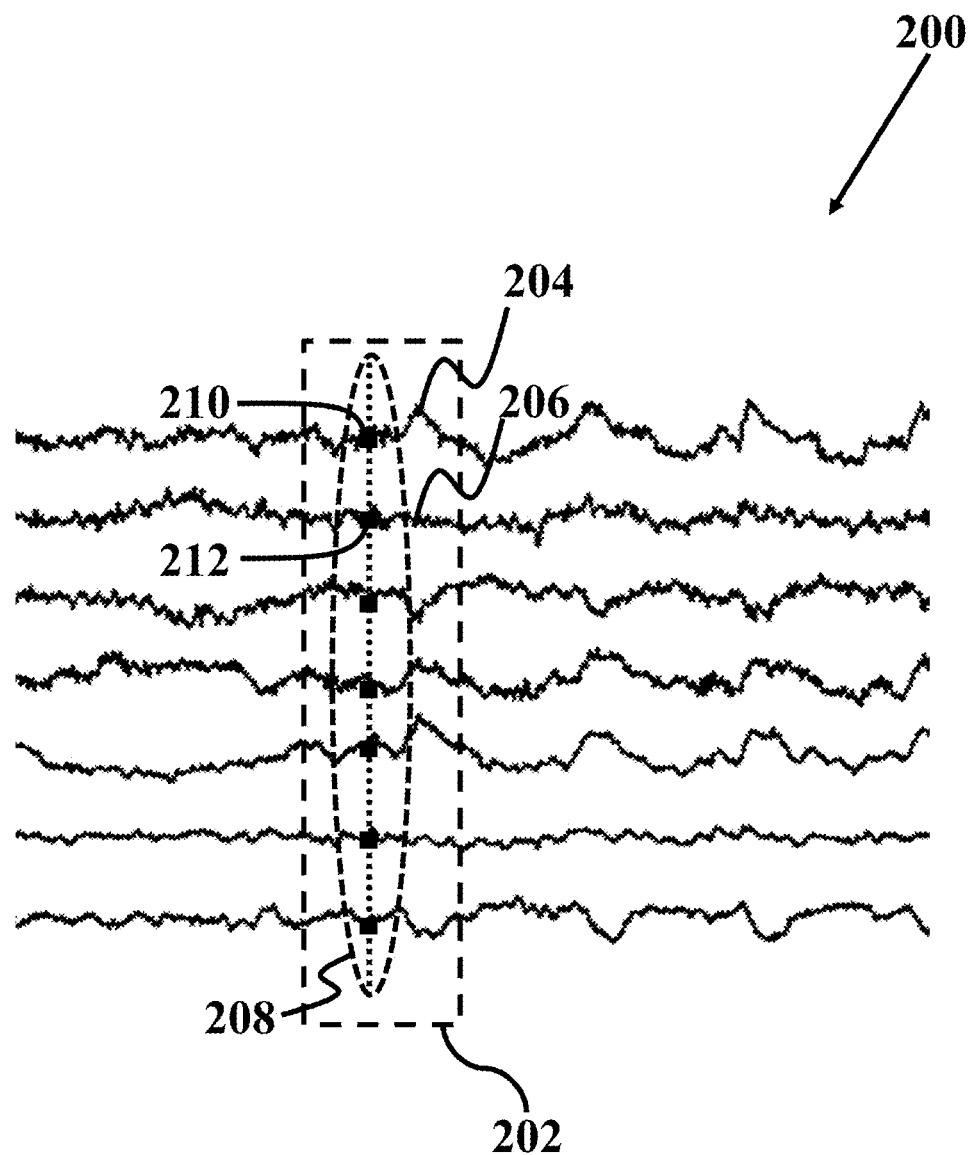
FIG. 2 shows an implementation of a plurality of signals according to one implementation of the present disclosure.

FIG. 2 shows an implementation of a plurality of signals 200, consistent with one or more implementations of the present disclosure. Referring to FIG. 2, in some implementations, preparing the plurality of vectors (the first step 118) may include extracting a plurality of epochs 202 from the plurality of signals 200, and extracting the plurality of vectors from the plurality of epochs 202. In some examples, the plurality of epochs 202 may include a first epoch 204 and a second epoch 206. Each of the plurality of epochs 202 may include a given number of samples of the plurality of samples. In addition, a vector 208 of the plurality of vectors may include a first sample 210 of the first epoch 204 and a second sample 212 of the second epoch 206. In an implementation, each of the plurality of epochs 202 $S(t;\xi_n)$ may be considered a wide sense stationary (WSS) and mean ergodic (ME) random and stochastic process subject to $t=m_s T$ (wherein, $m_s \in Z$, T is a sampling period over time, and is a related parameter for the stochastic process with a meaningful range of n).

Figure 3:
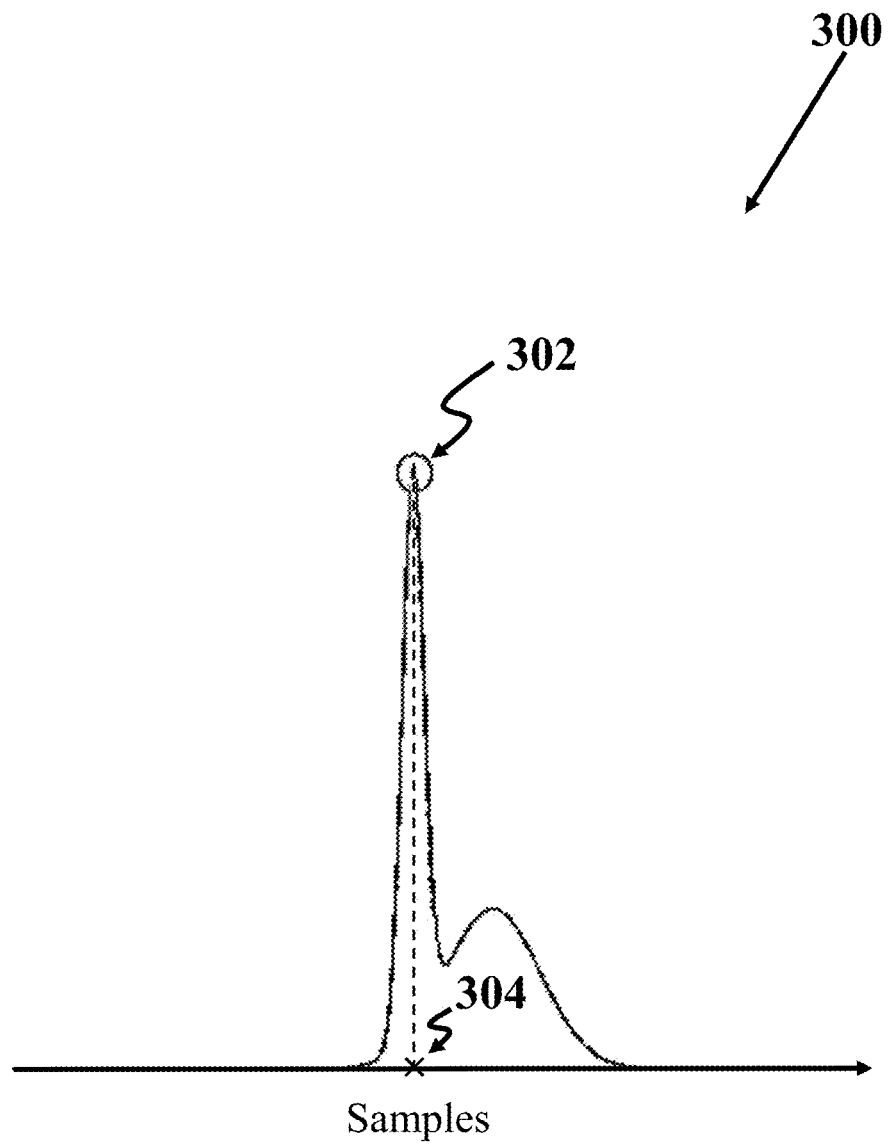
FIG. 3 shows an implementation of a multimodal ensemble probability density function according to one implementation of the present disclosure.

FIG. 3 shows an implementation of a multimodal ensemble probability density function (PDF) 300, consistent with one or more implementations of the present disclosure. In different implementations, the ensemble PDF 300 may be obtained via an ensemble-based estimation process from corresponding epoch samples of the plurality of epochs 202. Referring to FIG. 3, in some implementations, extracting the kernel (the second step 120) may include estimating the multimodal ensemble PDF 300 for the vector 208 by using an expectation maximization (EM) technique for a Gaussian mixture model (GMM) of the vector 208, and choosing a sample of the vector 208 with a maximum value 302 in the multimodal ensemble PDF 300 as the mode value 304 of the vector 208. By synchronizing the plurality of epochs 202, the multimodal ensemble PDF 300 can be obtained for aligned epoch samples at each specific time t. By employing the GMM along with the EM algorithm, multiple simple Gaussian models may be combined in one complex and ensemble multimodal PDF with two probable clusters.

Figure 1D:
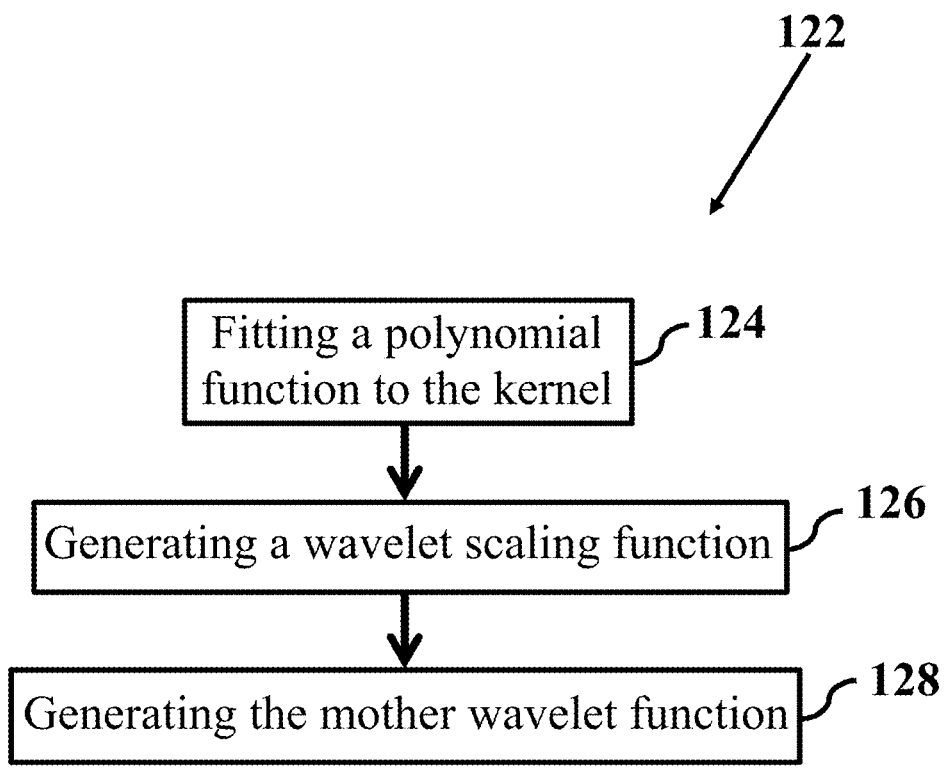
FIG. 1D is a flowchart of an implementation of extracting a mother wavelet function from a kernel according to one implementation of the present disclosure.

FIG. 1D is a flowchart of an implementation of the third step 122. In some implementations, extracting the mother wavelet function (third step 122) may include fitting a polynomial function to the kernel (a first step 124), generating a wavelet scaling function from the polynomial function (a second step 126), and generating the mother wavelet function from the scaling function (a third step 128).

In some implementations, the kernel may have a same length L as that of each of the plurality of epochs 202. Based on the Nyquist theorem and a limited frequency band-width of a discrete Fourier transform (DFT) of the kernel, the kernel may be modified by a downsampling procedure, considering $\underline{Ke}(e^{j\omega})=0$ for a frequency range $\omega_N \leq |\omega| \leq \pi$, where $\underline{Ke}(e^{j\omega})$ is a DFT of the kernel. To avoid aliasing, the downsampling may be accomplished with a rate of M, and the kernel $\hat{Ke}(n)$ may be efficiently and smoothly modified for $$n = 1, 2, \ldots, \frac{L}{M}.$$

Figure 4:
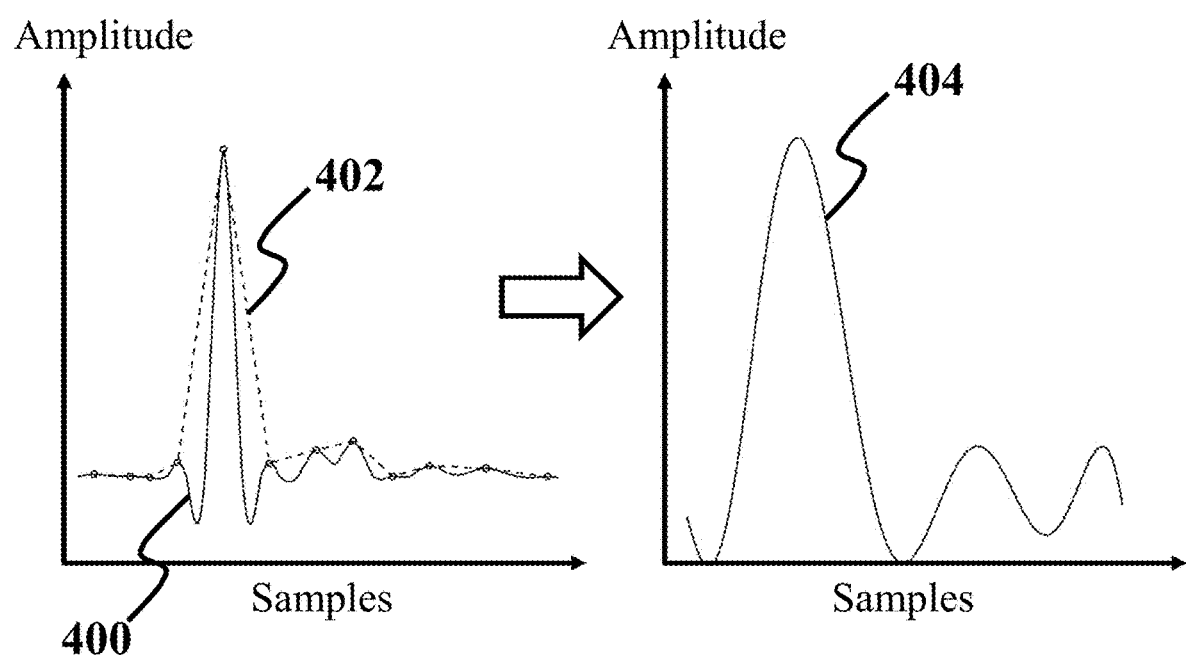
FIG. 4 shows an implementation of a resampled kernel according to one implementation of the present disclosure.

FIG. 4 shows an implementation of a resampled kernel 400, consistent with one or more implementations of the present disclosure. Referring to FIG. 4, in some implementations, fitting the polynomial function to the kernel (the first step 124) may include generating the resampled kernel 400 by resampling the kernel with a given resampling rate, generating a local maximum array 402, and fitting a Lagrange polynomial function 404 to the local maximum array 402. In an implementation, the local maximum array 402 may include a plurality of local maximum values of the resampled kernel 400.

In an implementation, the local maximum array 402 may be formed for N distinct samples of $\gamma_i$ as high-density and high singularity samples. For the set of these points, a unique Lagrange polynomial $L\tilde{K}e(\gamma)$ with a maximum order of N−1 may be interpolated by $$L\tilde{K}e(\gamma) = \sum_{i=1}^{N} \left\{ \underbrace{\prod_{j=1, i \neq j}^{N} \frac{(\gamma - \gamma_j)}{(\gamma_i - \gamma_j)}}_{\text{Lagrange Polynomials}} \right\} \cdot \tilde{K}e_i \qquad \text{Equation (1)}$$

where $\tilde{K}e_i$ is an $i^{th}$ local extremum for the corresponding $\gamma_i$, and N is the length of polynomial coefficients. Regarding the order of interpolations, undesired oscillations and amplitudes may occur between two successive samples $\gamma_i$ and $\gamma_{i+1}$. Therefore, in some implementations, $L\tilde{K}e(\gamma)$ may be normalized into closed interval of [0,1], to achieve comparable ranges, and a normalized function $L\tilde{K}e_N$ may be obtained as a deterministic interpolated polynomial of the resampled kernel 400, with an order of N−1.

The normalized interpolated function of $L\tilde{K}e_N$ may be considered an orthogonal basis for expanding each the plurality of epochs 202 $S(t;\xi_i) \in V_{j+1}$ for arbitrary values of i and the discrete time of $t=m_s T$. In discrete wavelet transform (DWT) computations, to avoid redundancy, scaling and translation factors may be converted into discrete forms of $a=a_0^m$ and $b=nb_0a_0^m$ as the scaling and translation parameters, respectively. Since in the dyadic scale of time-frequency plane is assumed $a_0=2$, m and n are used as scaling and shifting factors, respectively. Therefore, each the plurality of epochs 202 can be expanded by $$S(t;\xi_i) = \sum_k C_{j+1}(k) 2^{\frac{j+1}{2}} \frac{\varphi}{Norm}(2^{j+1}\gamma_i - k) \qquad \text{Equation (2)}$$

for $t = m_s T$ where $C_{j+1}$ is a projection (decomposition) coefficient of $S(t;\xi)$ on the sub-space $V_{j+1}$, and $\varphi(\cdot)$ is the scaling function. The parameter Norm is a normalization parameter. Therefore, a prefect set of $\varphi = \{2^{j/2} L\tilde{K}e_N (2^j\gamma_i - k)\}_{j,k \in Z}$ may be selected as a set of orthonormal basis functions for each of the plurality of epochs 202. The sub-space $V_{j+1}$ with the orthonormal bases can be considered a separable Hilbert space. Due to the following limitation for long-term signals:

$$\lim_{i \to \infty} \left\| S(t;\xi_i) - \sum_i \langle S(t;\xi_i), \varphi_i \rangle \cdot \varphi_i \right\| \to 0, \qquad \text{Equation (3)}$$

a set of $\{\varphi_i\}$ can include basis functions for the sub-space $V_{j+1}$. This limitation demonstrates that for decomposing each of the plurality of epochs 202 with regard to a limited length L, a finite number of coefficients can be sufficient. According to discrete forms of the scaling and translation parameters and Mallat's nested spaces, a sub-space $V_j$ can be defined as $$V_j = \text{Span}\{2^{j/2} L\tilde{K}e_N(2^j\gamma_i - k)\}_{j,k \in Z}.$$

According to the above discussion, in some implementations, generating the wavelet scaling function (the second step 126) may include generating a function $\varphi(\gamma)$ according to an operation defined by $$\varphi(\gamma) = 2^{j/2} p(2^j\gamma - k), \qquad \text{Equation (4)}$$

and normalizing the function $\varphi(\gamma)$ such that $\|\varphi(\gamma)\|=1$, where $\gamma$ is a variable, $p(\cdot)$ is the polynomial function, j and k are integer parameters, and $\|\cdot\|$ is an $l_2$ norm operator.

Figure 1E:
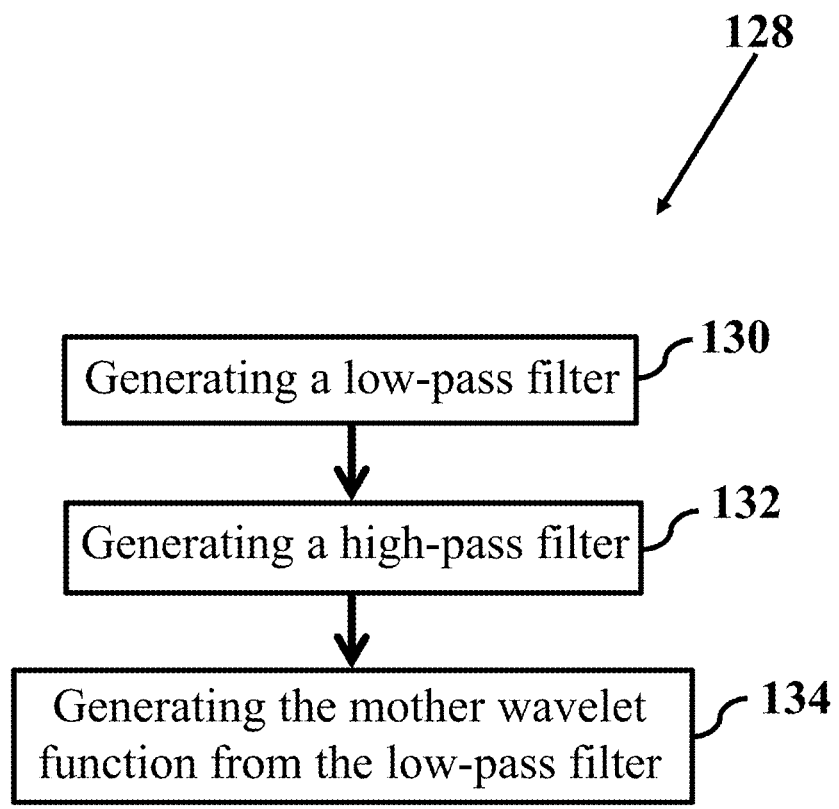
FIG. 1E is a flowchart of an implementation of generating a mother wavelet function from a scaling function according to one implementation of the present disclosure.

FIG. 1E shows a flowchart of an implementation of the third step 128. In some implementations, generating the mother wavelet function may include generating a low-pass filter from the wavelet scaling function (a first step 130), generating a high-pass filter from the low-pass filter (a second step 132), and generating the mother wavelet function from the high-pass filter (a third step 134).

In some implementations, generating the low-pass filter (the first step 130) may include calculating an inverse discrete Fourier transform (IDFT) of a function $\hat{H}(e^{j\omega})$ satisfying a condition according to:

$$\hat{\varphi}(e^{j\omega}) = \frac{1}{\sqrt{2}} \hat{H}(e^{j\frac{\omega}{2}}) \hat{\varphi}(e^{j\frac{\omega}{2}}), \qquad \text{Equation (5)}$$

where $\omega$ is an angular frequency, and $\hat{\varphi}(e^{j\omega})$ is a discrete Fourier transform (DFT) of the wavelet scaling function.

In an implementation, the wavelet scaling function $\varphi(t)$ and the Fourier transform $\hat{\varphi}(e^{j\omega})$ may be compactly supported functions with finite band-widths. The set of orthonormal basis functions $\{\varphi_i\}_{i \in N}$ can be expanded by a linear combination of computed scaling functions in a lower sub-space, as $$\varphi(2^j t - k) = \sum_n h_n \sqrt{2} \, \varphi(2^{j+1}t - 2k - n) \text{ for } t = m_s T \qquad \text{Equation (6)}$$

where $h_n$ is an $n^{th}$ coefficient of the low-pass filter. To determine $k_n$, some assumptions can be made as $$\sum_n h_n = \sqrt{2}, \qquad \text{Equation (7a),}$$

$$\sum_n |h_n|^2 = 1, \text{ and} \qquad \text{Equation (7b),}$$

$$\hat{\varphi}(e^{j\omega}) = \prod_k \left[ \frac{1}{\sqrt{2}} \hat{H}(e^{j\frac{\omega}{2^k}}) \right] \hat{\varphi}(e^{j0}), \qquad \text{Equation (7c),}$$

where $\hat{\varphi}(e^{j0})$ is a DC level for the DFT of the $\varphi(t)$ in the frequency domain, and $$\hat{H}(e^{j\omega}) = \sum_n h_n e^{-jn\omega}$$

for the low-pass filter. According to Equation (5), the magnitude of $\hat{H}(e^{j\omega})$ can be given by $$|\hat{H}(e^{j\omega})| = \sqrt{2} \left| \frac{\hat{\varphi}(e^{j2\omega})}{\hat{\varphi}(e^{j\omega})} \right|. \qquad \text{Equation (8)}$$

Therefore, $\hat{H}(e^{j\omega})$ can be obtained by numerical calculations. In some implementations, based on the coefficient $\sqrt{2}$ in Equations (5)-(8), the following relationship can be assumed for $\hat{H}(e^{j\omega})$ at finite samples as a DFT sequence for $-\pi \leq \omega \leq \pi$, $$|\hat{H}(e^{j\omega})|^2 + |\hat{H}(e^{j(\omega+\pi)})|^2 = 2 \qquad \text{Equation (9).}$$

Therefore, in some implementations, it can be assumed that $\hat{H}(e^{j0}) = \sqrt{2}$ and $\hat{H}(e^{j\pi}) = 0$. As a result, $h_n$ can be considered a periodic and causal finite impulse response (FIR) low-pass filter.

In some implementations, generating the high-pass filter (the second step 132) may include calculating a function g(n) based on a DC offset according to an operation defined by:

$$g(n) = (-1)^n h(N-1-n), \qquad \text{Equation (10)}$$

where n is a discrete time instant, N is an integer parameter, and h(•) is an N-point low-pass finite impulse response (FIR) filter.

Based on the Bochner's theorem, a Fourier transform of a kernel may be known as a kernel in the Reproducing kernel Hilbert space (RKHS). Accordingly, based on $$\sum_k |\hat{\varphi}(\omega + 2k\pi)|^2 = 1,$$

in some implementations, generating the mother wavelet function (the third step 134) may include a calculating a function $\hat{\psi}(e^{j\omega})$, according to operation defined by:

$$\hat{\psi}(e^{j\omega}) = \frac{1}{\sqrt{2}} \hat{G}\left(e^{j\frac{\omega}{2}}\right) \hat{\varphi}\left(e^{j\frac{\omega}{2}}\right), \qquad \text{Equation (11)}$$

and calculating an IDFT of the function $\hat{\psi}(e^{j\omega})$, where $\omega$ is an angular frequency, $\hat{G}(\bullet)$ is a DTF of the high-pass filter, and $\hat{\varphi}(\bullet)$ is a DFT of the wavelet scaling function.

In an implementation, the mother wavelet function $\psi(t) \in W_j$ can be defined over a complement space of $W_j$, where $V_j \perp W_j$, and these spaces may have one intersection on zero-vector with a definition of $V_{j+1} = V_j \oplus W_j$ as an error of mapping in the sub-space $V_j$.

Figure 5:
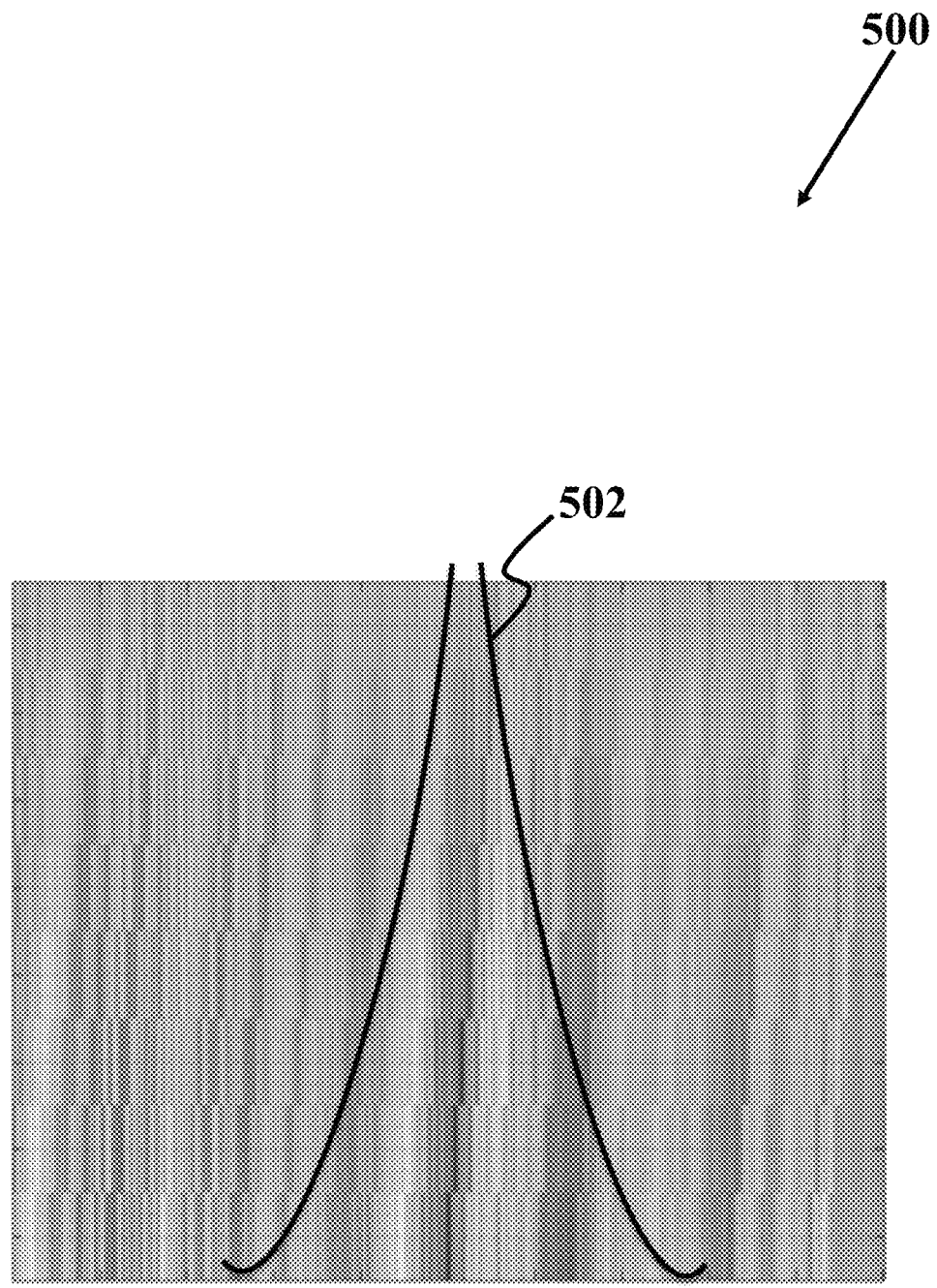
FIG. 5 shows an implementation of a cone of influence (COI) map according to one implementation of the present disclosure.

Referring again to FIG. 1B, the second step 114 may include extracting the COI of the wavelet transform. FIG. 5 shows an implementation of a COI map 500. In some implementations, the COI 502 may be obtained by applying the mother wavelet function $\hat{\psi}(e^{j\omega})$ on a signal of the plurality of signals 200. An implementation of a COI 502 is shown in FIG. 5. As shown in FIG. 5, in some implementations, the COI 502 may be conical shaped.

Figure 6:
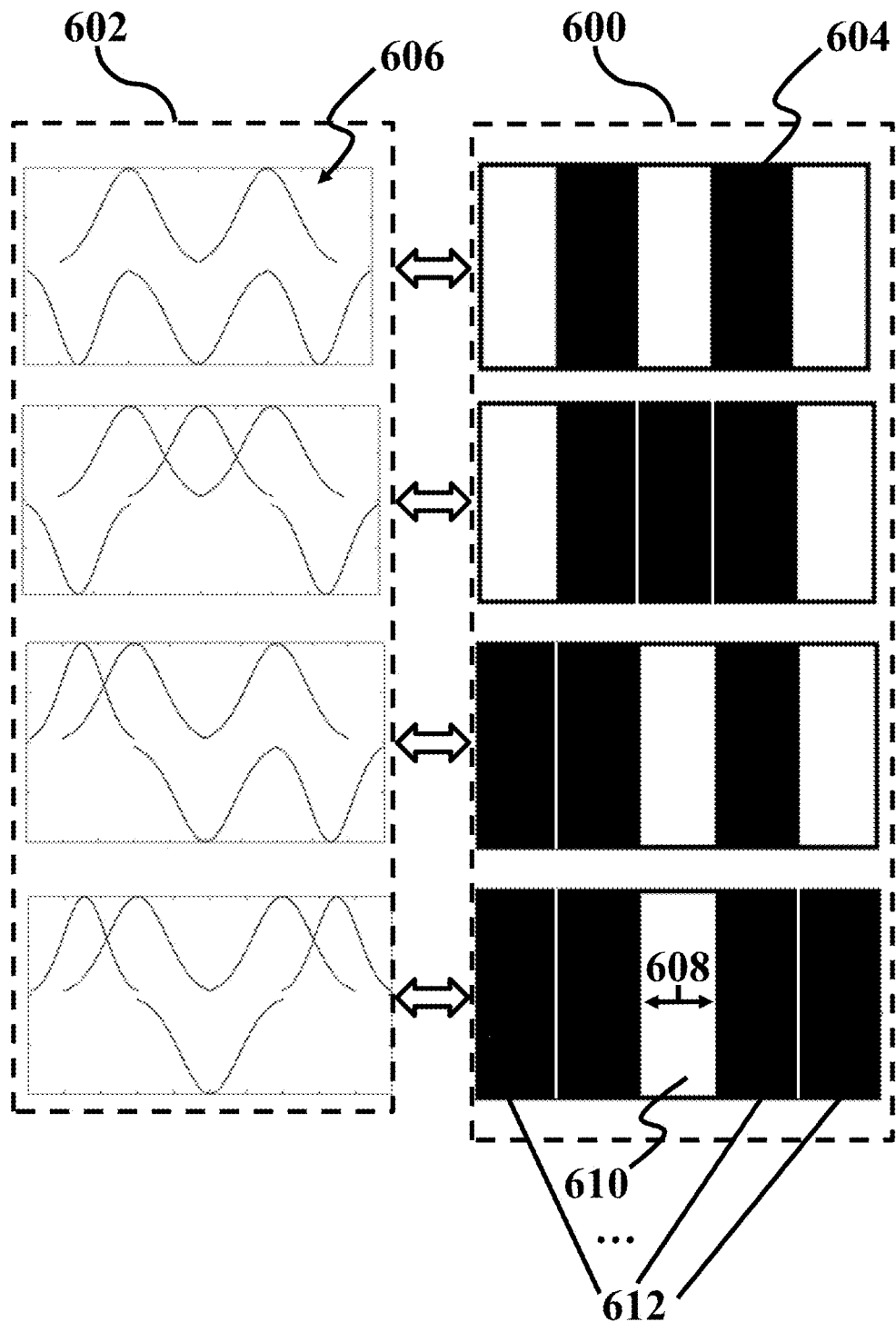
FIG. 6 shows an implementation of a plurality of patterns according to one implementation of the present disclosure.

FIG. 6 shows an implementation of a plurality of patterns 600 for modeling the COI 502. Each of the plurality of patterns 600 may be described by a combination of Gaussian functions of a plurality of Gaussian functions 602. For example, a pattern 604 of the plurality of patterns 600 may be described by a combination 606 of the plurality of Gaussian functions 602.

According to FIG. 6, in some implementations, generating the pattern (the third step 116) may include calculating a function $ptn_i^j(t)$ according to an operation defined by:

$$ptn_i^j(t) = \frac{C_{i,j}}{\sigma_{i,j}\sqrt{2\pi}} e^{-\frac{(t-\mu_{i,j})^2}{2\sigma_{i,j}^2}}, \qquad \text{Equation (12)}$$

where t is a time instant, $1 \leq i \leq I$ and $1 \leq j \leq J$ are integer parameters, I and J are given integer constants, $C_{i,j} \in \{-1, 1\}$ is a given constant associated with the pattern, $\mu_{i,j}$ is a given mean value of the function $ptn_i^j(t)$, $\sigma_{i,j}$ is a standard deviation of the function $ptn_i^j(t)$, and $\sigma_{i,j}^2$ is a variance of the function $ptn_i^j(t)$. The integer constant I may define the number of the plurality of patterns 600, and the integer constant J may define the number of Gaussian functions in the combination 606. In an implementation, $\Delta g_{i,j}$ may be determined based on a width 608 of a band 610 of a plurality of bands 612 in each of the plurality of patterns 600, and $\mu_{i,j}$ may determine an overlap percentage of successive Gaussian functions of Equation (12) in the combination 606. In another implementation, positive or negative amplitudes may be determined for each of the Gaussian functions by the constant $C_{i,j}$.

Figure 1F:
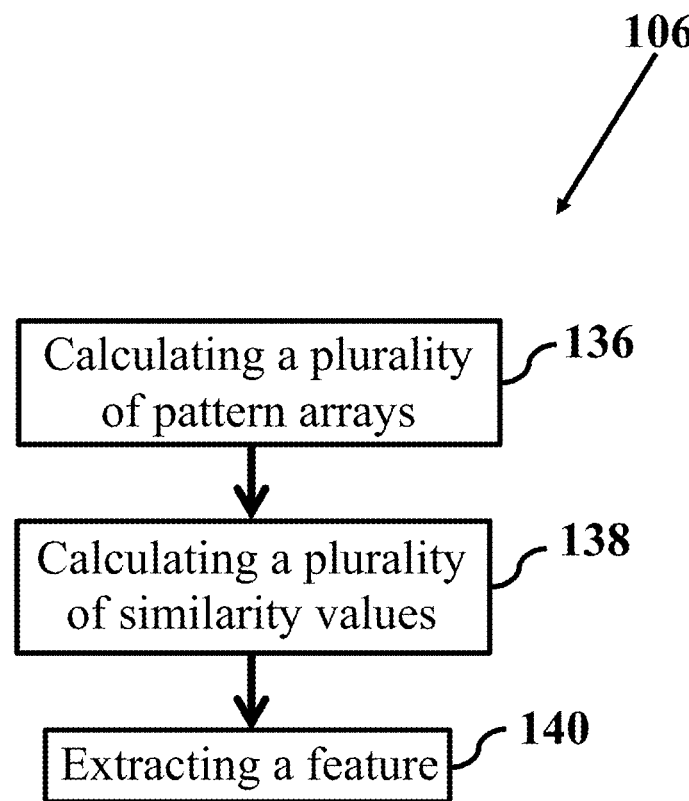
FIG. 1F is a flowchart of an implementation of extracting a plurality of features from a plurality of signals according to one implementation of the present disclosure.

FIG. 1F is a flowchart of an implementation of the third step 106. In some implementations, extracting the plurality of features (the third step 106) may include calculating a plurality of pattern arrays by applying the pattern 604 of the plurality of patterns 600 on a signal of the plurality of signals 200 (a first step 136), calculating a plurality of similarity values by measuring a similarity between successive pattern samples of a pattern array of the plurality of pattern arrays (a second step 138), and extracting a feature of the plurality of features from the plurality of similarity values based on a dispersion of the plurality of similarity values (a third step 140).

Figure 7:
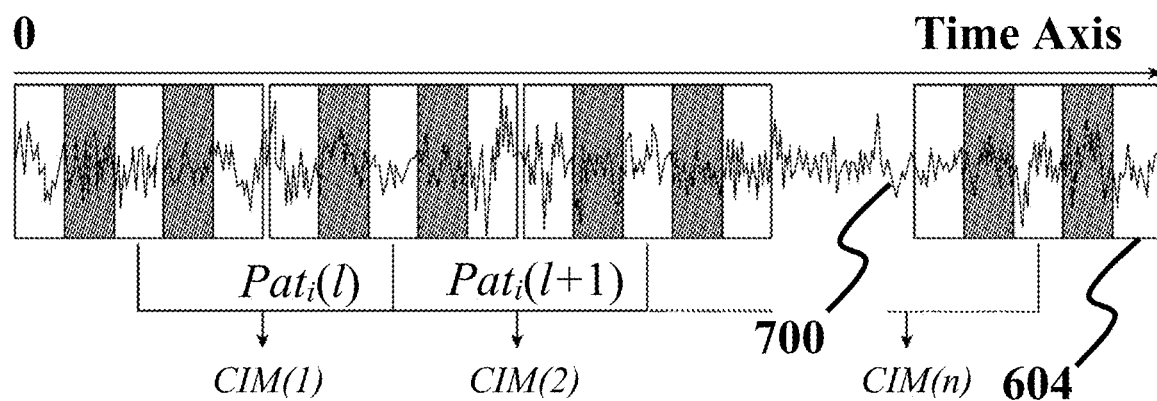
FIG. 7 shows an implementation of calculating a plurality of pattern arrays according to one implementation of the present disclosure.

FIG. 7 shows an implementation of calculating the plurality of pattern arrays by applying the pattern 604 on a signal 700 (the first step 136). In some implementations, calculating the plurality of pattern arrays (the first step 136) may include calculating a pattern array $Pat_i$ of the plurality of pattern arrays according to an operation defined by:

$$Pat_i(l) = \sum_{j=1}^{J} \left\{ \frac{1}{\Delta g_{i,j}} \sum_{t=\mu_{i,j}-\frac{\Delta g_{i,j}}{2}+1}^{\mu_{i,j}+\frac{\Delta g_{i,j}}{2}} ptn_i^j(t) \cdot S_l(t) \right\}, \qquad \text{Equation (13)}$$

where i, j, and l are integer parameters, and $S_l(t)$ is an $l^{th}$ segment of the signal 700. According to Equation (13), in an implementation, an $l^{th}$ pattern sample of the pattern array $Pat_i$ may be calculated by employing function $ptn_i^j(t)$ on the segment $S_l(t)$ of the signal 700. To obtain the next pattern sample, the function $ptn_i^j(t)$ may be shifted on the signal 700. Consequently, a separate pattern array of the plurality of pattern arrays may be obtained for each of the plurality of patterns 600.

In some implementations, calculating the plurality of similarity values (the second step 138) may include calculating a similarity value of the plurality of similarity values according to an operation defined by:

$$CIM_i(n) = \sqrt{Kr(0) - \hat{V}(Pat_i(l), Pat_i(l+1))}, \qquad \text{Equation (14)}$$

where n is an integer variable, $Kr(\bullet)$ is a Gaussian kernel, and $\hat{V}(Pat_i(l), Pat_i(l+1)) = E\{Kr(Pat_i(l) - Pat_i(l+1))\}$, where $Pat_i(l)$ is an $l^{th}$ pattern sample of an $i^{th}$ pattern array of the plurality of pattern arrays, $Pat_i(l+1)$ is an $(l+1)^{th}$ pattern sample of the $i^{th}$ pattern array of the plurality of pattern arrays, and $E\{\}$ is an expectation operator. In an example, the Gaussian kernel may be defined by $$Kr(x) = \frac{1}{\sigma\sqrt{2\pi}} e^{-\frac{x^2}{2\sigma^2}},$$

where x is a variable and σ is a Gaussian kernel standard deviation. In some cases, the Gaussian kernel may satisfy the Mercer's theorem.

According to Equation (14), in different implementations, the similarity value (CIM) may be calculated for every two successive pattern samples of $Pat_i(l)$ and $Pat_i(l+1)$, to evaluate dynamic ranges of the seizure and non-seizure signals. Therefore, this procedure may be repeated for every successive pair of the plurality of pattern arrays. In the end, the CIM series may be calculated based upon each of the plurality of patterns 600. The CIM measure may be considered a non-linear similarity-based measure between two random variables, based on the definitions of correlation and entropy. In other implementations, the CIM may be a non-negative, symmetric measure, and may be robust against outlier samples calculated from shifting procedures.

Figure 8:
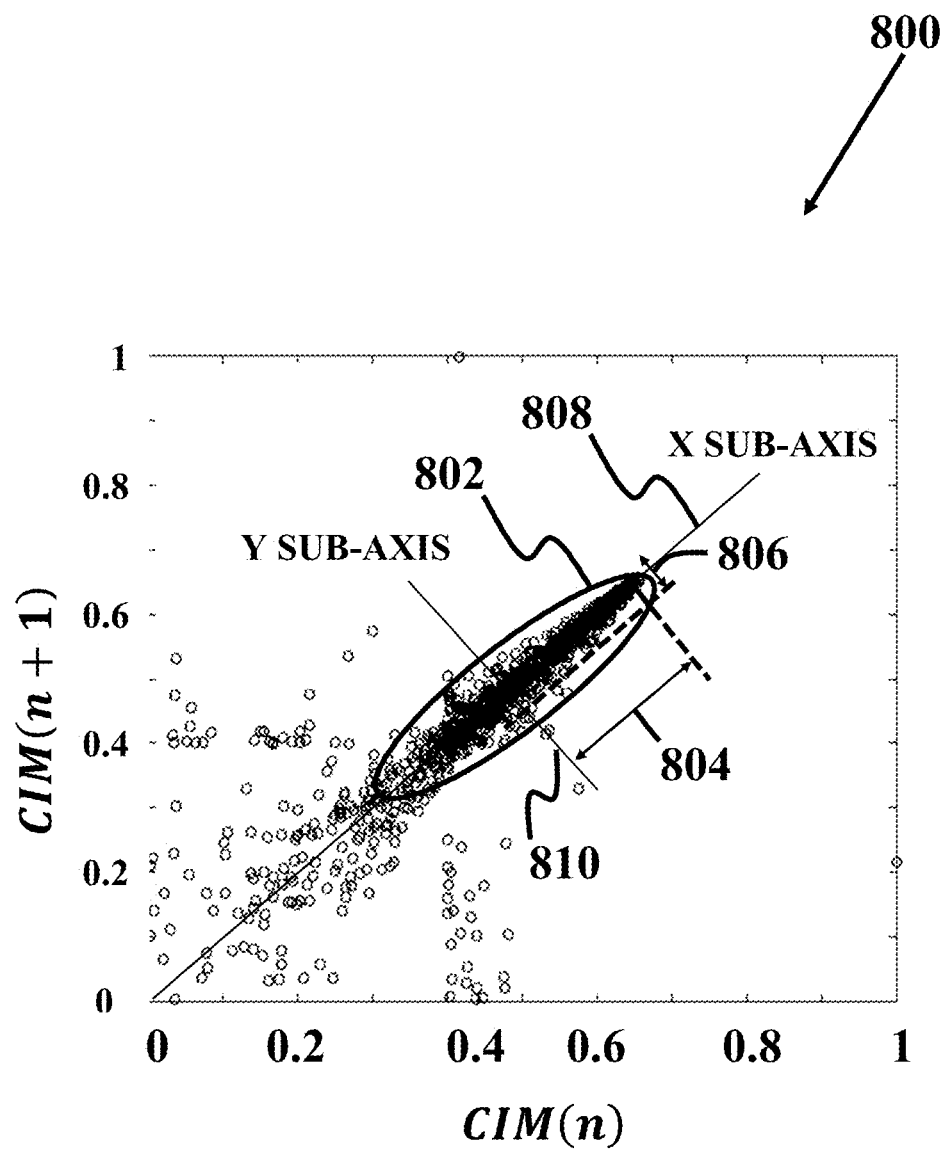
FIG. 8 shows an implementation of a Poincaré-based map according to one implementation of the present disclosure.

FIG. 8 shows an implementation of a Poincaré-based map 800, consistent with one or more implementations of the present disclosure. In some implementations, extracting the feature (the third step 140) may include plotting the Poincaré-based map 800 for the plurality of similarity values, fitting an ellipse 802 to the Poincaré-based map 800 by using a least squares (LS) technique, and calculating the feature according to an operation defined by:

$$CEF(i) = \frac{LR(i)}{SR(i)}, \quad \text{Equation (15)}$$

where i is an integer variable associated with the feature CEF(i), LR(i) is a first radius 804 of the ellipse 802, and SR(i) is a second radius 806 of the ellipse 802. The ellipse 802 may include a first axis 808 and a second axis 810. In an implementation, the first radius 804 may be along the first axis 808, and the second radius 806 may be along the second axis 810. In an example, the parameter i may correspond to the pattern 604. Equation (15) may define a dispersion criterion concluded from the mapped CIM data to the Poincaré-based map 800. In different implementations, a separate value for the feature CEF (i) may be extracted from each segment of the signal 700 for each of the plurality of patterns 600.

Referring to FIG. 8, in an implementation, for each of the plurality of patterns 600, the Poincaré-based map 800 of CIM (n+1) may be plotted based on an alternating flip of CIM (n). The Poincaré-based map 800 may be used for distinguishing chaotic and random behavior of the CIM series. In different implementations, the LS estimation technique may be employed for error minimization on a convenient cost function to fit the ellipse 802 with a minimum error on the Poincaré-based map 800 from the CIM series.

To achieve an acceptable time of processing, a suitable order of complexity, and acceptable detection and prediction performances, the parameters and structures of different stages of the method 100 may be optimized. In some implementations, optimizing the plurality of patterns and the plurality of features (the third step 106) may include repeating an optimization process until a termination condition is satisfied. In an implementation, the termination condition may include one of a number of repetitions of the optimization process reaching a repetition threshold and a convergence error being smaller than a convergence threshold. In other words, the optimization process may be terminated if variations of optimized values for the plurality of patterns and the plurality of features in successive repetitions of the optimization process become smaller than the convergence threshold, or the number of the repetitions of the optimization process exceeds the repetition threshold.

Figure 9:
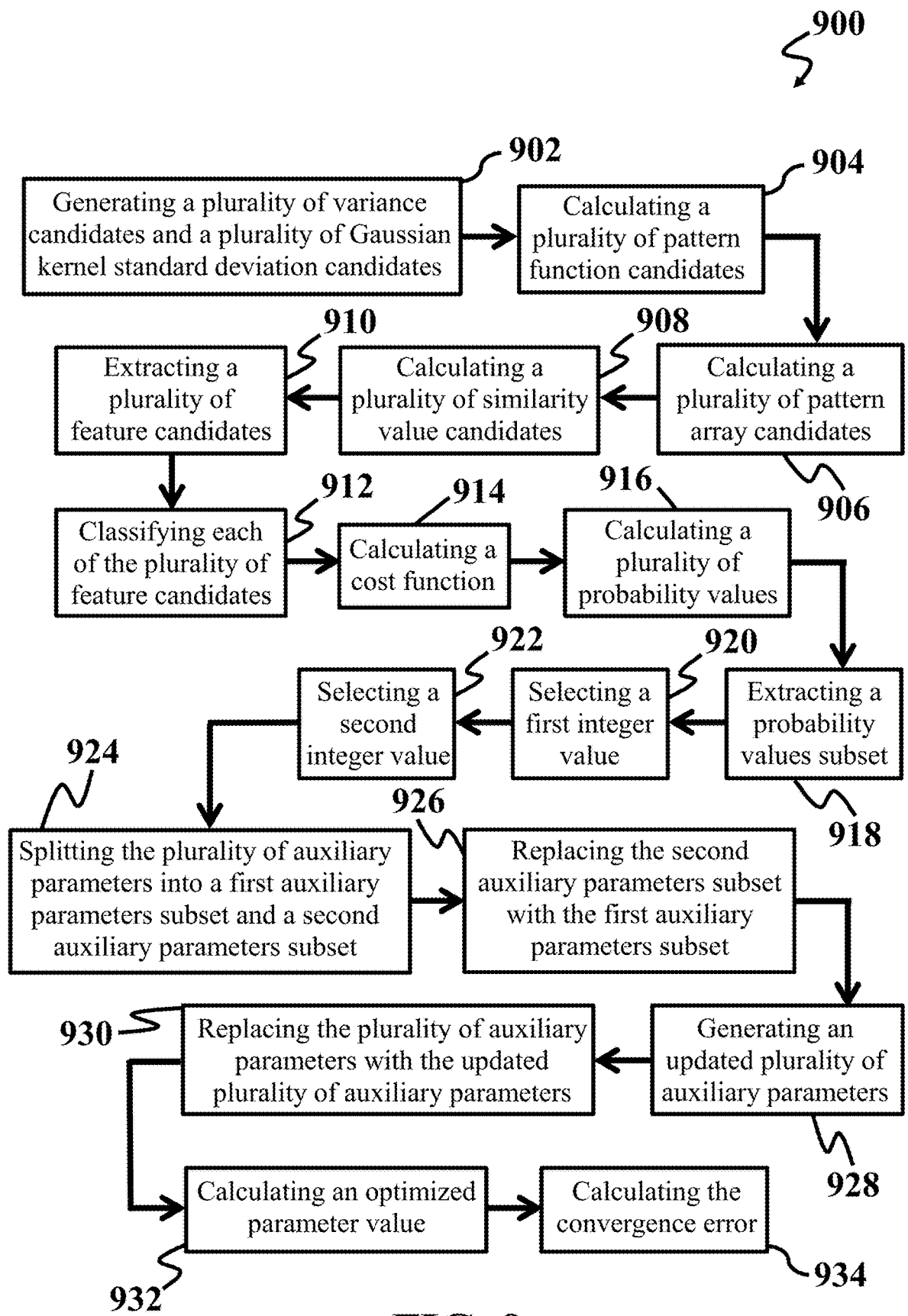
FIG. 9 shows a flowchart of an implementation of an optimization process according to one implementation of the present disclosure.

FIG. 9 is a flowchart of an implementation of the optimization process 900. In some implementations, the optimization process may include generating a plurality of variance candidates and a plurality of Gaussian kernel standard deviation candidates for a plurality of integer values of an integer parameter k∈[1,$N_k$] (a first step 902), where $N_k$ is the number of the plurality of variance candidates, calculating a plurality of pattern function candidates $ptn_{i,j}^k(t)$ for the plurality of integer values of the integer parameter k (a second step 904), calculating a plurality of pattern array candidates $Pat_i^k$ (a third step 906), calculating a plurality of similarity value candidates $CIM_i^k(n)$ for the plurality of integer values of the integer parameter k (a fourth step 908), extracting a plurality of feature candidates from the plurality of similarity value candidates (a fifth step 910), classifying each of the plurality of feature candidates in the seizure class and the non-seizure class by applying an Elman recurrent neural network classifier on the plurality feature candidates (a sixth step 912), calculating a cost function CF(k) for classification results of the Elman recurrent neural network classifier for each of the plurality of integer values of the integer parameter k (a seventh step 914), calculating a plurality of probability values $P^k(\delta^k)$ for a plurality of auxiliary parameters $\delta^k$ (an eighth step 916), extracting a probability values subset from the plurality of probability values (a ninth step 918), selecting a first integer value $D_{min}$ from the plurality of integer values (a tenth step 920), selecting a second integer value $D_{max}$ from the plurality of integer values (an eleventh step 922), splitting the plurality of auxiliary parameters $\delta^k$ into a first auxiliary parameters subset and a second auxiliary parameters subset (a twelfth step 924), replacing the second auxiliary parameters subset with the first auxiliary parameters subset (a thirteenth step 926), generating an updated plurality of auxiliary parameters (a fourteenth step 928), replacing the plurality of auxiliary parameters with the updated plurality of auxiliary parameters (a fifteenth step 930), calculating an optimized parameter value by averaging the plurality of auxiliary parameters (a sixteenth step 932), and calculating the convergence error by calculating a difference of a maximum value of the plurality of auxiliary parameters and a minimum value of the plurality of auxiliary parameters (a seventeenth step 934).

In some implementations, calculating the plurality of pattern function candidates (the second step 904) may include calculating $ptn_{i,j}^k(t)$ according to a set of operations defined by:

$$ptn_{i,j}^k(t) = \frac{C_{i,j}}{\sigma_{i,j,k}\sqrt{2\pi}} e^{-\frac{(t-\mu_{i,j})^2}{2\sigma_{i,j,k}^2}}, \quad \text{Equation (16)}$$

where t is a time instant, 1≤i≤I and 1≤j≤J are integer parameters, and $\sigma_{i,j,k}^2$ is a variance candidate of the plurality of variance candidates.

In different implementations, calculating the plurality of pattern array candidates (the third step 906) may include calculating $Pat_i^k$ according to a set of operations defined by:

$$Pat_i^k(l) = \sum_{j=1}^{J} \left\{ \frac{1}{\Delta g_{i,j}} \sum_{t=\mu_{i,j}-\frac{\Delta g_{i,j}}{2}+1}^{\mu_{i,j}+\frac{\Delta g_{i,j}}{2}} ptn_{i,j}^k(t) \cdot S_l(t) \right\}, \quad \text{Equation (17)}$$

where $\text{Pat}_i^k(l)$ is an $l^{th}$ pattern sample candidate of an $i^{th}$ pattern array candidate of the plurality of pattern array candidates.

In an implementation, calculating the plurality of similarity value candidates (the fourth step 908) may include calculating $\text{CIM}_i^k(n)$ according to a set of operations defined by:

$$CIA_i^k(n) = \sqrt{(Kr^k(0) - \hat{V}^k(\text{Pat}_i^k(l), \text{Pat}_i^k(l+1)))}, \quad \text{Equation (18)}$$

where n is an integer variable, and $Kr^k(\cdot)$ is a Gaussian kernel candidate of a plurality of Gaussian kernel candidates. In an example, the Gaussian kernel candidate may be defined by:

$$Kr^k(x) = \frac{1}{\sigma_k \sqrt{2\pi}} e^{-\frac{x^2}{2\sigma_k^2}}, \quad \text{Equation (19)}$$

where x is a variable and $\sigma_k$ is a Gaussian kernel standard deviation candidate of the plurality of Gaussian kernel standard deviation candidates, and $$\hat{V}^k(\text{Pat}_i^k(l), \text{Pat}_i^k(l+1)) = E\{Kr^k(\text{Pat}_i^k(l) - \text{Pat}_i^k(l+1))\}. \quad \text{Equation (20)}$$

In some implementations, the sixth step 912 may include applying the Elman recurrent neural network classifier on the plurality feature candidates. The Elman classifier may include a 2-layer back propagation system with a feedback from an output of a hidden layer to its input. The feedback may facilitate recognition of temporal patterns and vectors with time-variant structures. In an example, the Elman classifier may classify the plurality of feature candidates to the seizure class and the non-seizure class. In a case, by employing an Nguyen-Widrow function, weights and biases may be initialized and the Elman classifier may be trained for classification. In addition, the cost function $CF(k)$ may be defined as a mean square error (MSE) of Elman classification results at each iteration of the optimization process 900.

In some implementations, calculating the plurality of probability values (the eighth step 916) may include calculating $P^k(\delta^k)$ according to a set of operations defined by:

$$P^k(\delta^k) = \frac{(\delta^k)^\alpha \cdot CF(k)^\beta}{\sum_{k=1}^{N_k} (\delta^k)^\alpha \cdot CF(k)^\beta}, \quad \text{Equation (21)}$$

where $\alpha$ and $\beta$ are given constants that may be meta-heuristic and may be arbitrarily selected. In different implementations, these parameters may be optimized iteratively for selecting a best state in the optimization process 900. In an implementation, $\alpha$ may be set to 3 and $\beta$ may be set to 2 to achieve a small classification error. The plurality of auxiliary parameters $\delta^k$ may be associated with the plurality of integer values of the integer parameter k, and may include one of the plurality of variance candidates $\sigma_{i,j,k}^2$ and the plurality of Gaussian kernel standard deviation candidates $\sigma_k$. In an example, the cost function $CF(k)$ may be considered as a part of fitness-function to evaluate the optimization process 900.

In an implementation, the probability values subset may include a probability value of the plurality of probability values, and may be larger than half of the plurality of probability values. In a case, the first integer value $D_{min}$ may be associated with a first element with a minimum value in the probability values subset, and the second integer value $D_{max}$ may be associated with a second element with a maximum value in the probability values subset. In different implementations, an auxiliary parameter in the first auxiliary parameters subset may be associated with the probability value.

In some implementations, generating the updated plurality of auxiliary parameters (the fourteenth step 928) may include combining the first auxiliary parameters subset and the second auxiliary parameters subset to obtain the updated plurality of auxiliary parameters, and updating each of the updated plurality of auxiliary parameters according to an operation defined by:

$$\delta_{new}^k = \left| \delta^k + \frac{LVRA(D_{min}, D_{max})}{b_N} - a_N \right|, \quad \text{Equation (22)}$$

where $a_N$ and $b_N$ are normalization parameters and $LVRA(D_{min}, D_{max})$ is a random number between the first integer value $D_{min}$ and the second integer value $D_{max}$. In an implementation, the random number $LVRA(D_{min}, D_{max})$ may be generated by using a Las Vegas randomized algorithm.

Referring again to FIG. 1A, in some implementations, the fifth step 110 may include applying the plurality of cascaded AdaBoost classifiers on the plurality of features. In an implementation, a positive class by label '1' may be assumed for the seizure class, and a negative class by label '-1' may be assumed for the non-seizure class. In addition, each of the plurality of cascaded AdaBoost classifiers may be properly trained based on some limitation hypotheses around weak learner functions. Each weak classifier may be selected based on a detection error. In an example, the detection error may be less than 0.5 ($\varepsilon_{Nt} < \frac{1}{2}$). In a next stage of learning, a confidence coefficient $\varepsilon_{Nt}$ may be computed as a performance measure for each weak classifier. Furthermore, the weights of the plurality of cascaded AdaBoost classifiers may be iteratively updated by employing a normalization factor such that the summation of all weights equal 1 per iteration. Henceforward, this algorithm may be repeated to satisfy the stopping condition of $\varepsilon_{Nt} < \frac{1}{2}$ in the weak classifiers. In an implementation, a final employed strong decision function may be based on a linear combination of weak classifier functions. In different implementations, a cascade structure may be employed and a sub-feature vector may be passed from all stages. In another implementation, the cascade structure may recognize a label of an input signal as a seizure or a non-seizure signal.

Referring again to Equation (12), in some implementations, the plurality of cascaded AdaBoost classifiers may be used for determining the value of $\mu_{i,j}$ based on suitable overlaps of the Gaussian functions in the combination 606. In an example, the plurality of cascaded AdaBoost classifiers may be evaluated for different values of the overlaps and different numbers of the plurality of cascaded AdaBoost classifiers. For example, by using a trial and error approach on the plurality of cascaded AdaBoost classifiers, the value of $\kappa$ may be set to 0.1, and the number of the plurality of cascaded AdaBoost classifiers may be set to 41.

Figure 10:
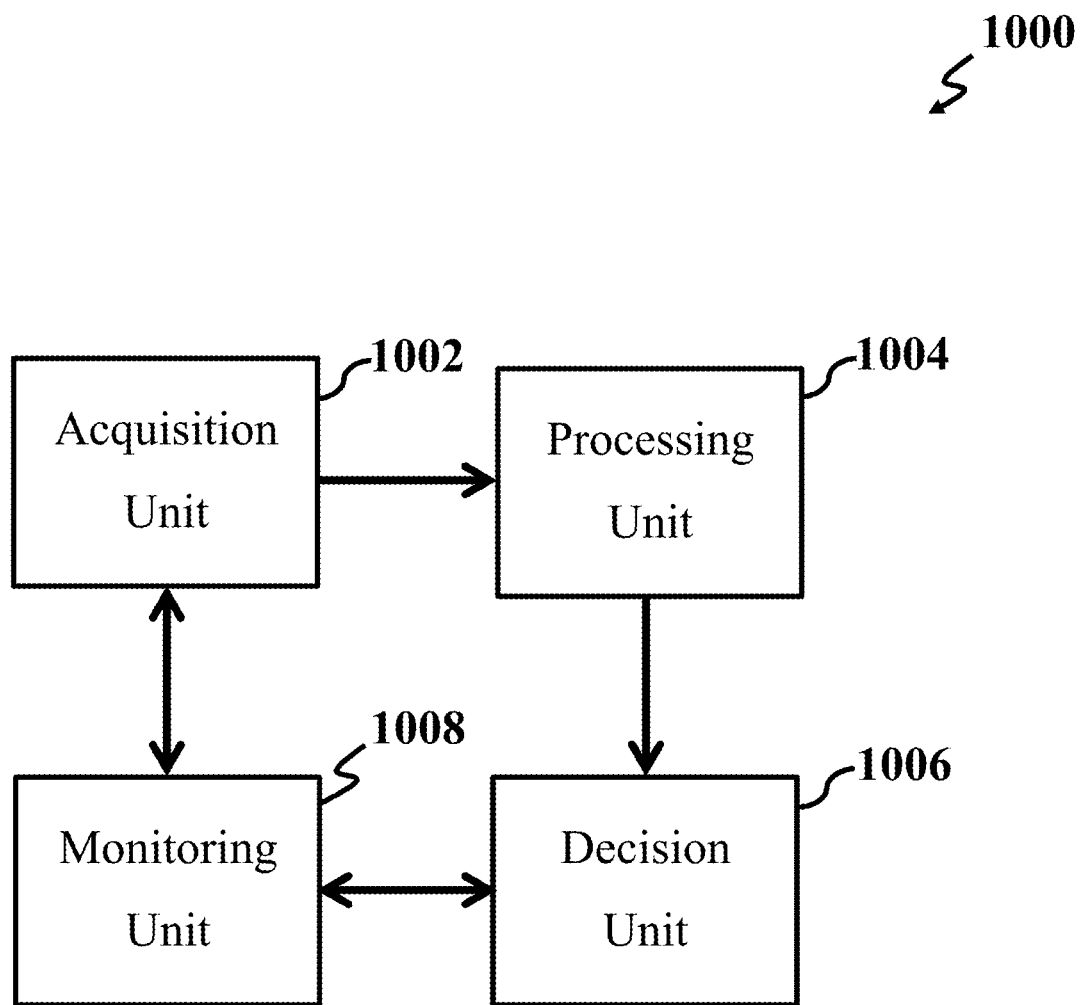
FIG. 10 shows a block diagram of an implementation of a system for detecting and predicting an epileptic seizure according to one implementation of the present disclosure.

FIG. 10 shows a block diagram of an implementation of a system 1000 for detecting and predicting an epileptic seizure. In some implementations, the system may include an acquisition unit 1002, a processing unit 1004, a decision unit 1006, and a monitoring unit 1008. In an implementation, the acquisition unit 1002 may include a plurality of electroencephalography (EEG) electrodes connected to a scalp of a patient. The plurality of EEG electrodes may include an EEG electrodes subset. In an implementation, the EEG electrodes subset may be configured to acquire a plurality of EEG signals via a plurality of EEG channels, and to band-pass filter each of the plurality of EEG signals based on a Kaiser-Bessel windowing procedure. In another implementation, the processing unit 1004 may be configured to calculate a wavelet transform of an EEG signal of the plurality of EEG signals, extract a cone of influence (COI) of the wavelet transform, generate a pattern according to the COI, calculate a plurality of pattern arrays by applying the pattern on the EEG signal, calculate a plurality of similarity values by measuring a similarity between successive sample of a patent array of the plurality of pattern arrays, extract a feature of the plurality of features from the plurality of similarity values based on a dispersion of the plurality of similarity values, and classify the EEG signal in a class of a plurality of classes by applying a plurality of cascaded AdaBoost classifiers on the plurality of features. In an example, the plurality of classes may include a seizure class and a non-seizure class. In some implementations, the decision unit 1006 may be configured to determine a medical treatment according to the class of the EEG signal. In other implementations, the monitoring unit 1008 may be configured to monitor variations of the EEG signal and send a feedback to the decision unit and the acquisition unit according to the variations of the EEG signal.

In different implementations, the acquisition unit 1002 may be configured to update the EEG electrodes subset by replacing an element in the EEG electrodes subset with an EEG electrode of the plurality of EEG electrodes according to the feedback from the monitoring unit 1008 unit. In addition, the decision unit 1006 may be configured to update the medical treatment according to the feedback from the monitoring unit 1008.

In different implementations, there may exist an optimal EEG electrodes subset for generating an optimal mother wavelet function for seizure detection and prediction. The optimal EEG electrodes subset may be chosen based on the history of the patient in seizure focus, age, type of epileptic seizure, and the number of involved EEG channels. In some implementations, the system 1000 may be tested on a new patient with a different type of epileptic seizure disorder. Based on the results, the EEG electrodes subset may be modified to achieve a new optimal EEG electrodes subset, and consequently a new optimal mother wavelet function for the new patient.

In some implementations, the processing unit 1004 may be implemented on a customized digital signal processing (DSP) unit, for example a field programmable gate array (FPGA), to increase the processing speed. According to Equation (15), the number of features may be selected equal to the number of the plurality of patterns 600. In some implementations, a limited number of patterns (for example, four patterns in FIG. 6) may efficiently describe different variations of seizure and non-seizure states of EEG signals. Therefore, in different implementations, the number of features may be considerably reduced, compared to the number of features in conventional seizure detection systems. Moreover, since the wavelet transform may indirectly influence the seizure detection process through the plurality of patterns 600, the wavelet calculations for feature extraction may be removed, resulting in a reduction of required adders and multipliers for FPGA implementation of the processing unit 1004. Therefore, in an implementation, an optimal FPGA implementation of seizure detection may be obtained in terms of computations and speed.

EXAMPLE 1

In this example detecting an epileptic seizure from multichannel EEG signals via an implementation of the method 100 is demonstrated. Scalp EEG signals were collected from 23 pediatric patients. The subjects had intractable seizure disorders and had been waiting to make an interventional decision for surgery actions. This dataset included 844 hours of the EEG signals and 163 seizure attacks with sampling frequency of 256 Hz and 16-bit resolution. The dataset was divided into two separated subsets. The first subset was used for extracting a mother wavelet function, and the second subset was used for designing an implementation of the method 100. Therefore, approximately 50% of the dataset with 18-channel EEG signals was selected randomly for the first subset. The remaining EEG signals of this dataset with 7-channel (selected as optimal channels) were applied to evaluate the method 100, and also for designing an implementation of the optimization process 900.

With regard to the unbalanced dataset and window-by-window signal segmentation, the ratio of the seizure to non-seizure epochs was selected approximately equal to the original EEG dataset to provide real and operational conditions in the evaluation of the method 100.

The sampling frequency of based on an A/D converter was 256 Hz with 16-Bit resolution. The duration of the recordings in the dataset was about 1 hour. Each of the recorded EEG signals was segmented into 30 second epochs. In addition to hardware filtering, to enhance the signal to noise ratio, a Kaiser-Bessel windowing procedure was employed after signal acquisition.

Based on the international 10-20 montaging system and bi-polar electrodes on the subjects's scalp, an 18-channel collection of 'FP1-F7', 'F7-T7', 'T7-P7', 'P7-O1''FP1-F3', 'F3-C3', 'C3-P3', 'P3-O1', 'FP2-F4', 'F4-C4', 'C4-P4', 'P4-O2', 'FP2-F8', 'F8-T8', 'T8-P8', 'P8-O2', 'FZ-CZ,' and 'CZ-PZ' was considered as the first collection.

To design a seizure detection system and also to increase the generalization capability for detecting various seizure types in different patients, seven channels of 'FP1-F7', 'FP2-F8', 'C3-P3', 'C4-P4', 'FZ-O1', 'P3-O1' and 'P8-O2' were selected. By using these pairs of electrodes, the summation of nerve cells activities contaminated all over the brain, especially for an epileptic seizure attack, may be described.

Referring again to FIG. 6, in this example, the plurality of patterns 600 and the plurality of Gaussian functions 602 were selected as the diagrams shown in FIG. 6. The number of the plurality of patterns 600 were set to 4, and each of the plurality of patterns 600 were described by a combination of 5 Gaussian functions. Corresponding to the number of the plurality of patterns 600, four pattern arrays were calculated by:

$$Pat_i(l) = \sum_{j=1}^{5}\left[\frac{1}{|b_j - a_j + 1|}\sum_{t=a_j}^{b_j} ptn_i^j(t - a_j + 1).S_{j,l}(t)\right], \quad \text{Equation (23)}$$

where $S_{j,l}(t)$ is a $j^{th}$ part of an $l^{th}$ segment of an EEG signal $S_l(t)$, corresponding to a $j^{th}$ band of each of the plurality of patterns 600 (represented in FIG. 6 by the band 610), $a_j$ is a $j^{th}$ element of the vector a, given by:

$$a = \left[1, (L_1 - A_1 + 1), \left(1 + \sum_{j=1}^{2} L_j - \sum_{j=1}^{2} A_j\right)\right]$$

Figure 11:
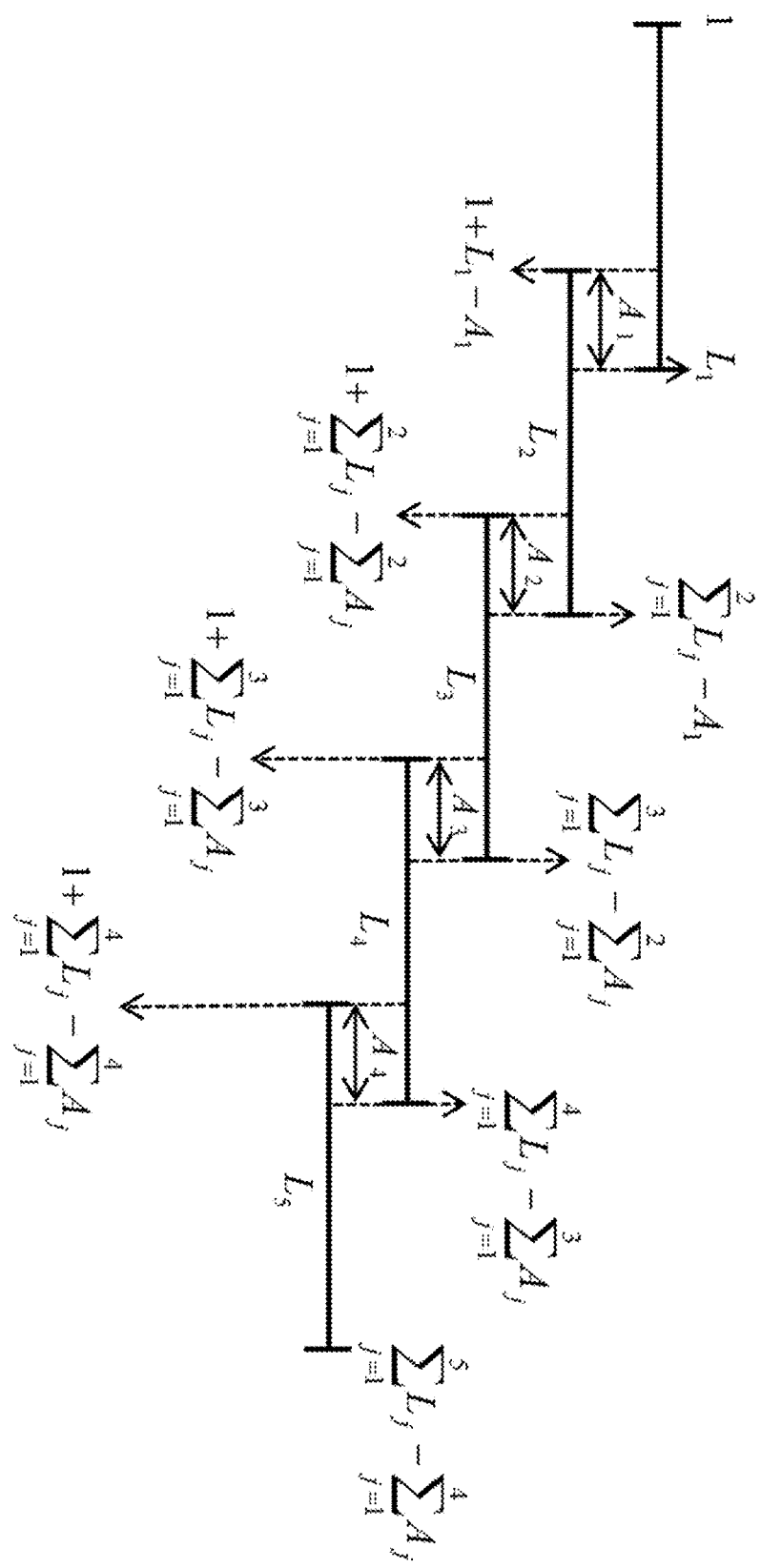
FIG. 11 is a schematic representing a relationship between a plurality of pattern parameters according to one implementation of the present disclosure.

-continued $$\left(1+\sum_{j=1}^{3} L_j - \sum_{j=1}^{3} A_j\right), \left(1+\sum_{j=1}^{4} L_j - \sum_{j=1}^{4} A_j\right)\right],$$

and $b_j$ is a $j^{th}$ element of the vector b, given by:

$$b = \left[L_1, \left(\sum_{j=1}^{2} L_j - A_1\right), \left(\sum_{j=1}^{3} L_j - \sum_{j=1}^{2} A_j\right),\right.$$

$$\left.\left(\sum_{j=1}^{4} L_j - \sum_{j=1}^{3} A_j\right), \left(\sum_{j=1}^{5} L_j - \sum_{j=1}^{4} A_j\right)\right],$$

where $L_j$ is the length of the Gaussian function $ptn_i^j(t)$, and $A_j$ is a length of an overlapping part of $ptn_i^j(t)$ and $ptn_i^{j+1}(t)$. The parameters $a_j$ and $b_j$ determine the length of each of the plurality of Gaussian functions 602 that is applied on $S_i(t)$. Comparing Equation (23) with Equation (13) shows that $\Delta g_{i,j} = |b_j - a_j + 1|$ in this example. FIG. 11 is a schematic representing the relationship between $a_j$ and $b_j$ for $1 \leq j \leq J$ with respect to $L_j$ and $A_j$.

Figure 12:
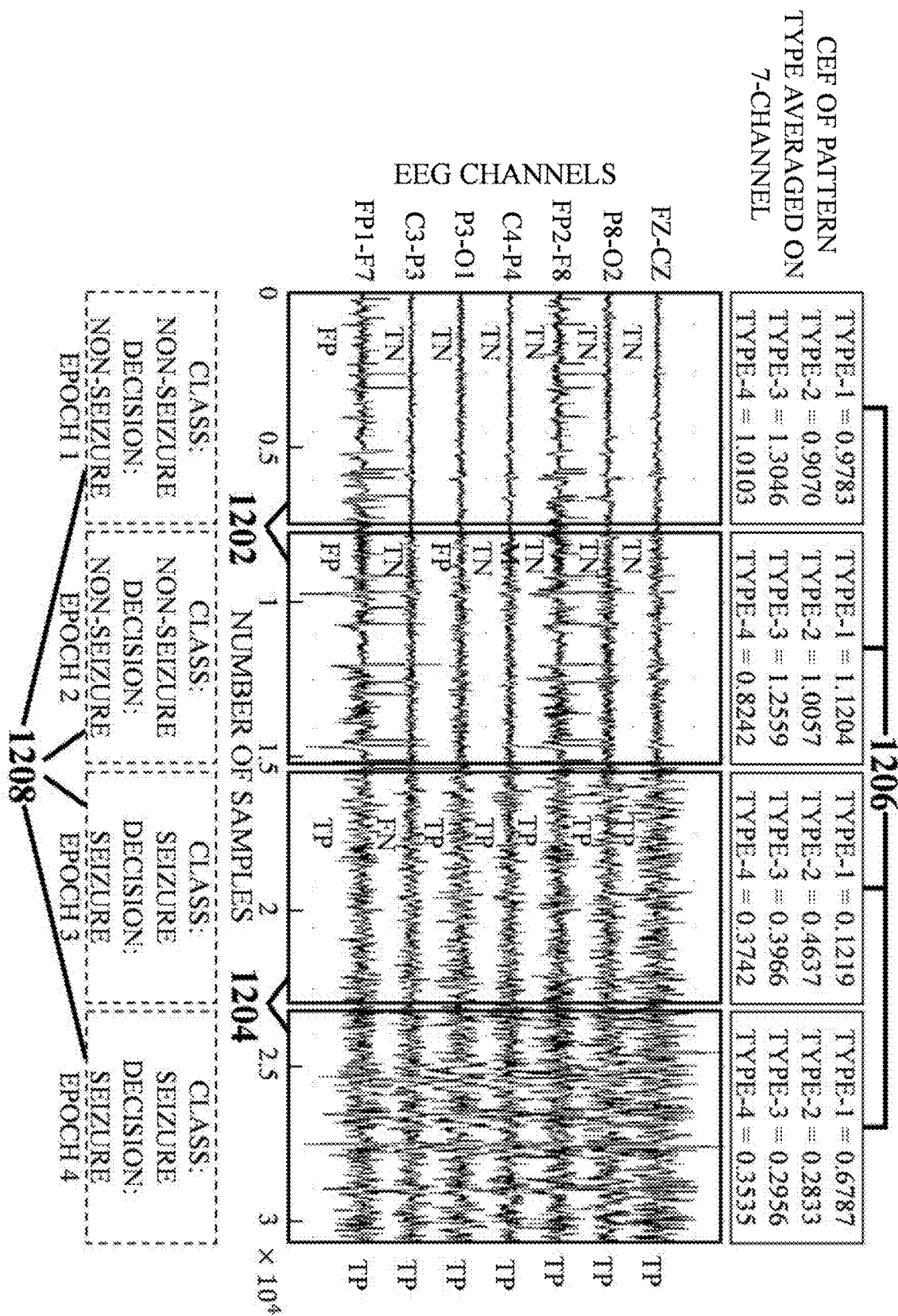
FIG. 12 shows four 30-second epochs according to one implementation of the present disclosure.

FIG. 12 shows four 30-second epochs (totally 2 minutes) on the 7 selected channels of the EEG signals as an example of detection results and patient's monitoring. The first two epochs 1202 belonged to the non-seizure class and the second two epochs 1204 belonged to the seizure class. For each epoch of these time-series, a plurality of averaged values 1206 of the feature CEF(i) over the 7 channels, and a plurality of decision classification results 1208 for each epoch are shown in FIG. 12. In this example, the method 100 was implemented on a personal computer (PC) with an Intel Core i7 CPU and a 6 GB of RAM, resulting in a computation time of about 0.168 seconds per each 30-second epoch for analyzing and classifying each epoch in the seizure and non-seizure classes.

To evaluate the performance of the method 100, a number of measures including true positive (TP) for correctly classified seizure (positive), true negative (TN) for correctly classified non-seizure (negative) samples, false positive (FP) for incorrectly classified seizure samples, and false negative (FN) for incorrectly classified non-seizure samples, were used.

Table 1 includes a definition of each of the plurality of measures. Referring to Table 1, the accuracy rate (ACC) is a convenient measure for a normal distributed dataset with a balance ratio between two categories. To test the repeatability and reproducibility of a test valuation, the precision rate and recall (or sensitivity) rate are frequently used. To analyze a seizure detection performance on an unbalanced EEG dataset, other tools such as G-Mean, F$_i$-Score and Van Rijsbergen's effectiveness measures are applied. In Table 1, the Van Rijsbergen's effectiveness measure is calculated based on a parameter $\alpha = 1/(1+\beta^2)$, where $\beta = 1$ in this example. Type I and Type II errors, borrowed from statistical hypothesis testing, are defined based on recall and specificity. In addition to the plurality of measures, in Table 1, a false detection rate (FDR) per hour ($h^{-1}$) is also used for evaluating the method 100 in this example. Table 2 shows the classification result and the mean value of the averaged values 1206 over all of the plurality of patterns 600, for each epoch. Table 3 shows the averaged evaluation results of the method 100 on multiple EEG channels according to the measure of Table 1 in this example.

TABLE 1

The measures for evaluating the method for detecting and predicting seizure.

| Measure | Formulation | Measure | Formulation |
| --- | --- | --- | --- |
| Accuracy Rate | $\frac{TP + TN}{TP + TN + FP + FN}$ | $F_1$-Score | $2 \cdot \frac{Precision \cdot Recall}{Precision + Recall}$ |
| Precision Rate | $\frac{TP}{TP + FP}$ | Van Rijsbergen's effectiveness measure | $1 - \frac{1}{\frac{\alpha}{Precision} + \frac{1-\alpha}{Recall}}$ |
| Recall (Sensitivity Rate) | $\frac{TP}{TP + FN}$ | Type I Error | $1 - \underbrace{\frac{TN}{TN + FP}}_{Specificity} = \frac{FP}{TN + FP}$ |
| G-Mean | $\sqrt{Sensitivity \times Specificity}$ | Type II Error | $1 - \underbrace{\frac{TP}{TP + FN}}_{Recall} = \frac{FN}{TP + FN}$ |

TABLE 2

Classification result and mean value of CEF for each epoch.

| | Epoch 1 | | Epoch 2 | | Epoch 3 | | Epoch 4 | |
| --- | --- | --- | --- | --- | --- | --- | --- | --- |
| | Feature values | Detection results | Feature values | Detection results | Feature values | Detection results | Feature values | Detection results |
| | 1.0501 | TN | 1.0516 | TN | 0.3391 | TP | 0.4028 | TP |

TABLE 3

Average evaluation results of the method for detecting and predicting seizure.

| Precision (%) | Recall (%) | Accuracy (%) | $F_1$-Score (%) | G-Mean (%) | Type I Error | Type II Error | Van Rijsbergen's Effectiveness Measure | FDR ($h^{-1}$) |
|---|---|---|---|---|---|---|---|---|
| 97.40 | 93.56 | 91.67 | 95.44 | 68.35 | 0.4047 | 0.0648 | 0.0456 | 0.015 |

EXAMPLE 2

In this example, creating an implementation of the mother wavelet function from a first EEG signal and reconstructing the first EEG signal using a corresponding discrete wavelet transform (DWT) is demonstrated. The first EEG signal is recorded from a 9-year-old female patient for approximately 31 hours using one model of channel montaging system and 31 separated recordings with 3 seizure events.

Figure 13:
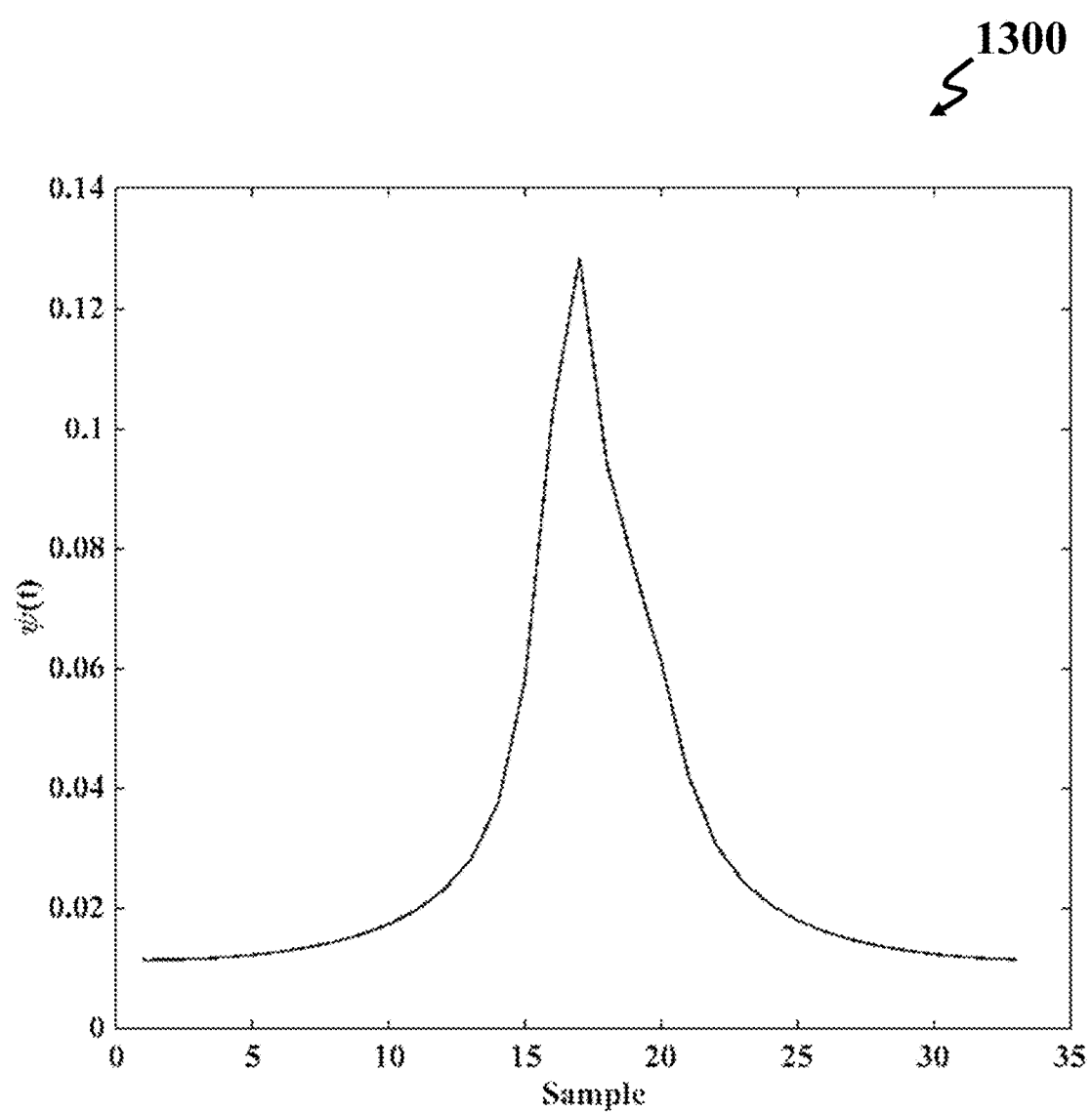
FIG. 13 shows an epoch obtained by windowing an electroencephalography (EEG) signal.

FIG. 13 shows an original epoch 1300 that is obtained by windowing the first EEG signal from an FZ-CZ EEG channel for 60 seconds (i.e., 15360 samples based on a sampling frequency of 256 Hz and a 16-bit resolution). The original epoch 1300 is selected so that the non-seizure, seizure and also an onset event (a non-seizure to a seizure transition state) are observable in the original epoch 1300. After some preprocessing such as applying a band-pass filter, the original epoch 1300 is prepared for processing.

Figure 14:
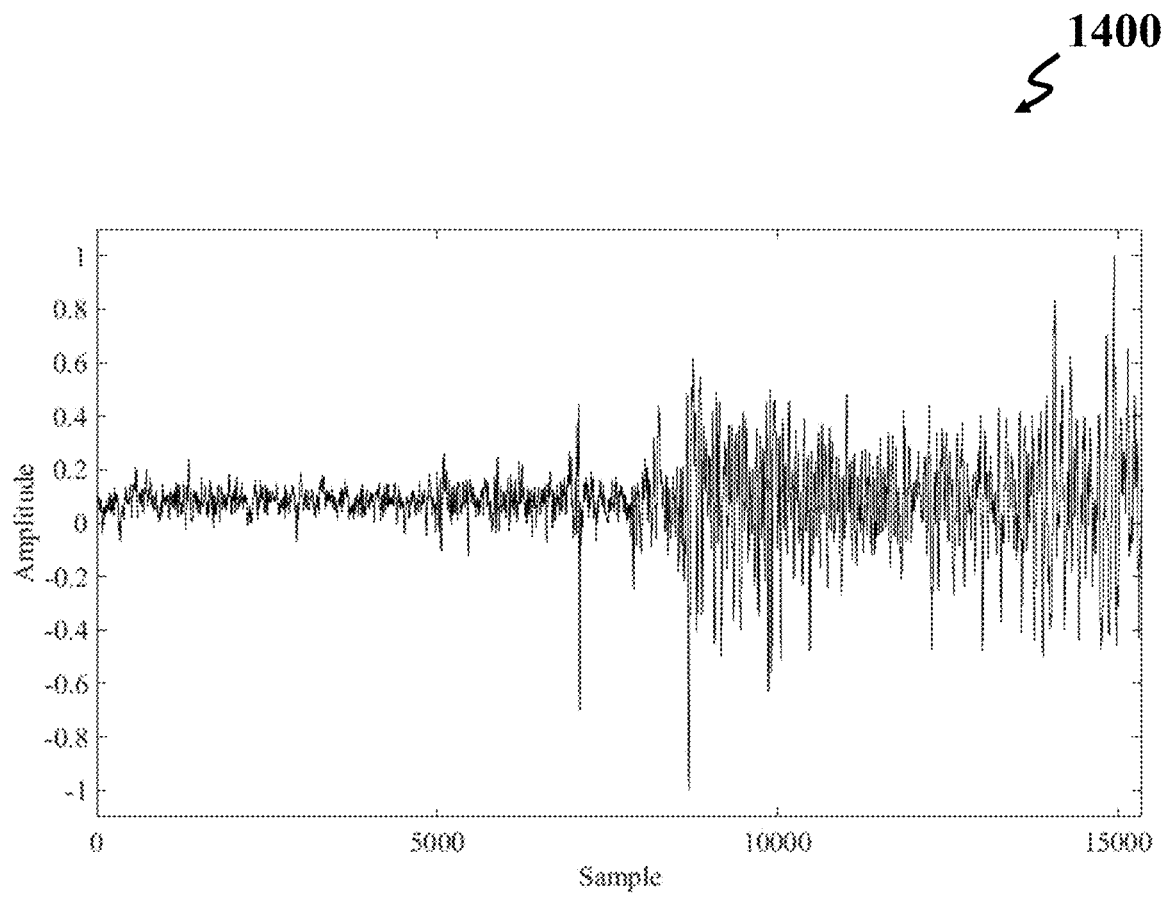
FIG. 14 shows a reconstructed epoch obtained by applying a discrete wavelet transform (DWT) on an original epoch and perfect reconstructing the original epoch by an inverse DWT.
Figure 15:
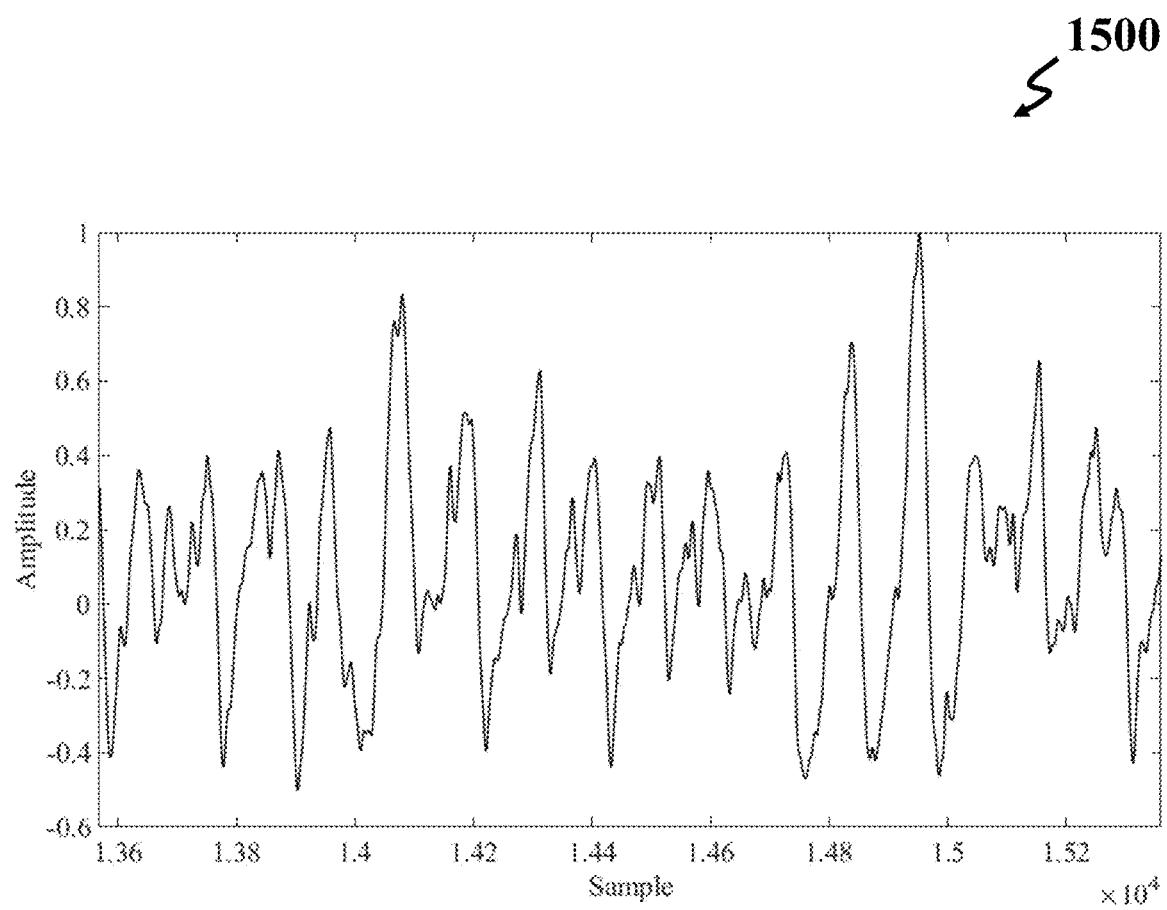
FIG. 15 shows a first segment of an original epoch from a seizure state.
Figure 16:
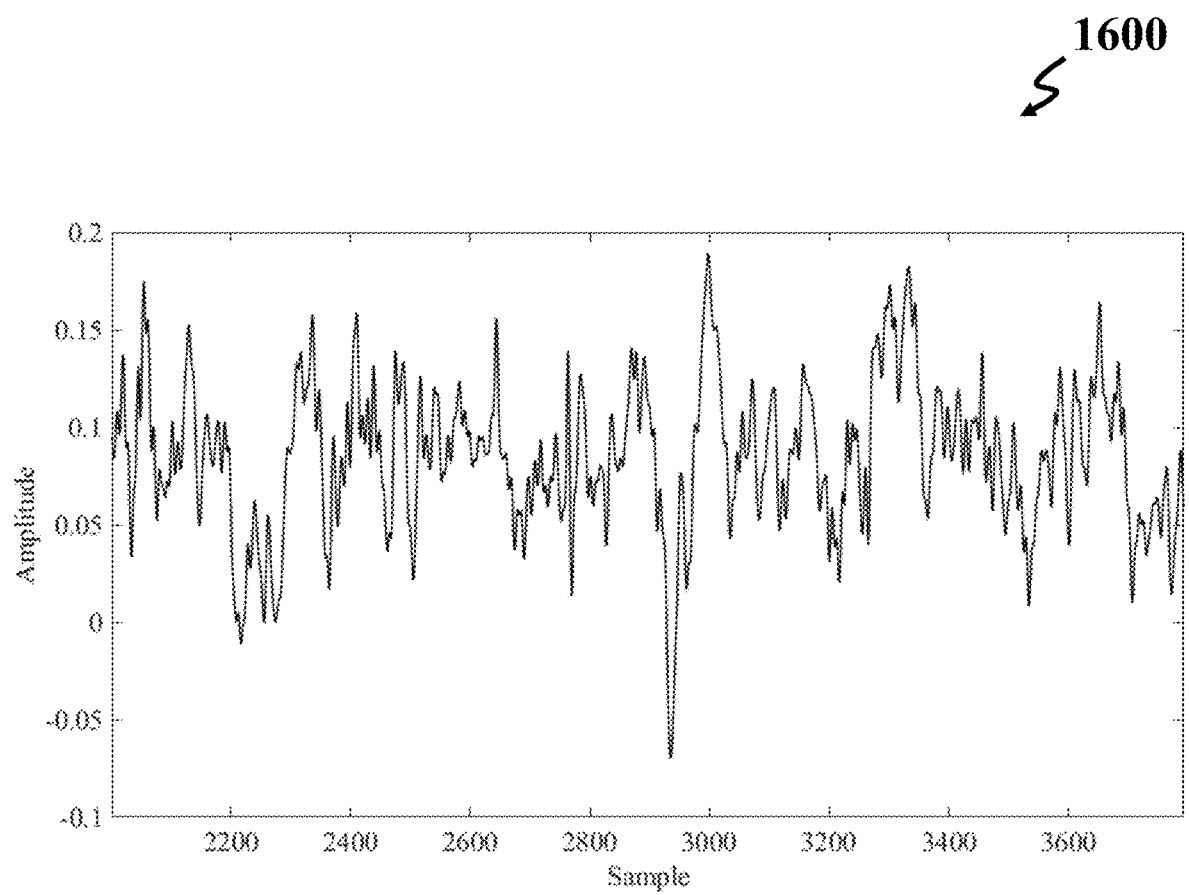
FIG. 16 shows a second segment of an original epoch from a non-seizure state.
Figure 17:
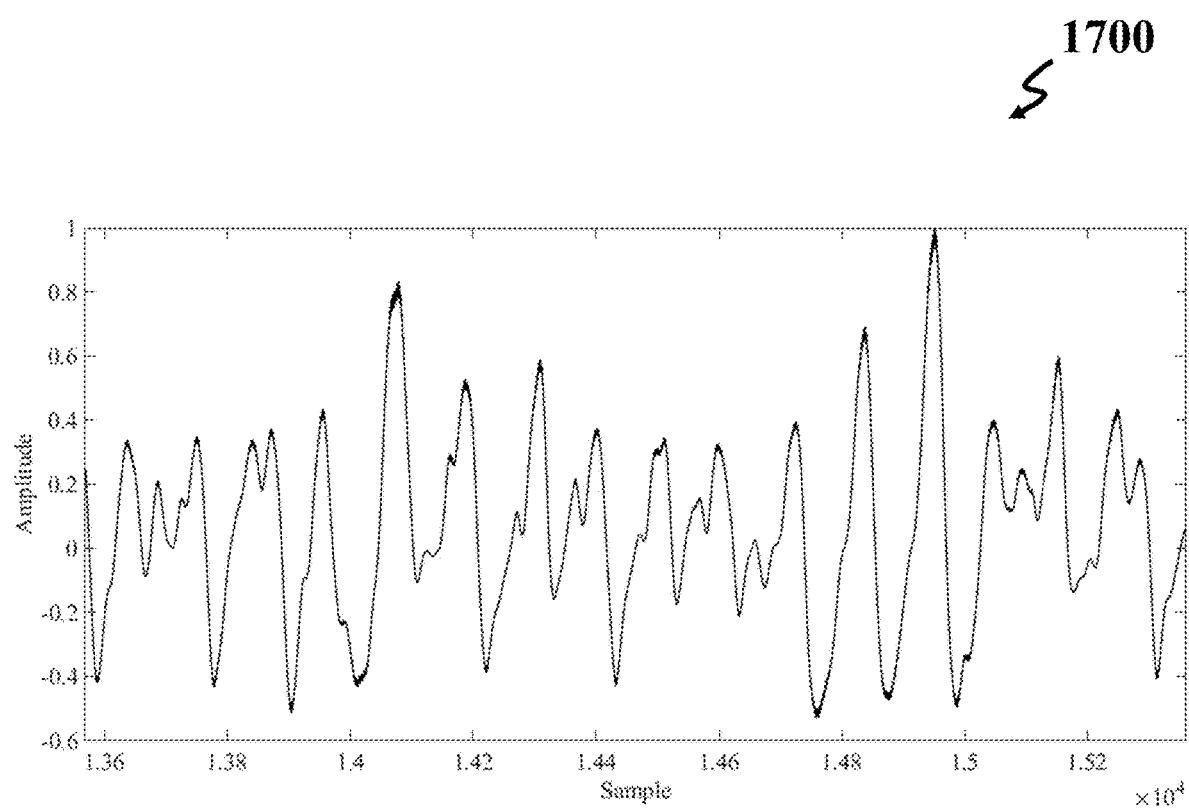
FIG. 17 shows a first reconstructed sample of a first segment of an original epoch.
Figure 18:
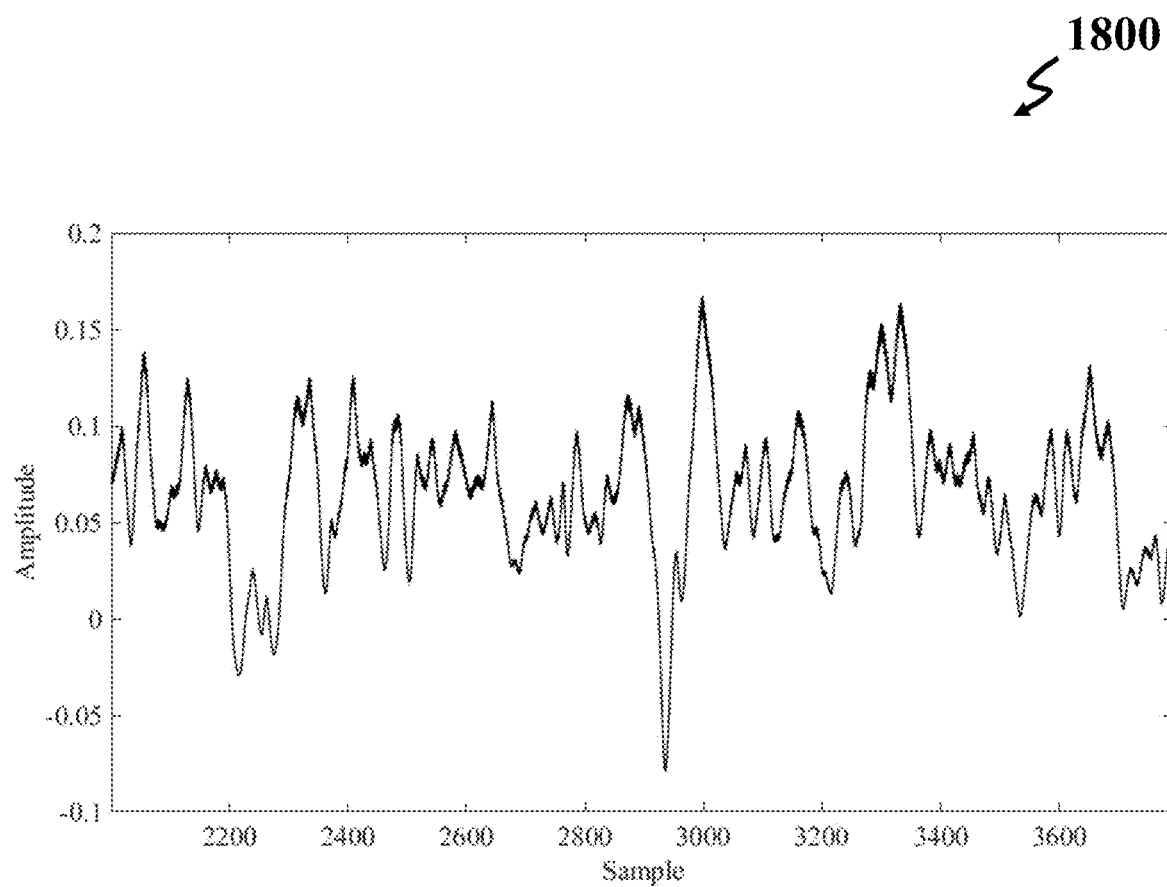
FIG. 18 shows a second reconstructed sample of a second segment of an original epoch.

FIG. 14 shows a reconstructed epoch 1400 that is obtained by applying the DWT in 1-level of decomposition and perfect reconstructing the original epoch 1300 by an inverse DWT. FIG. 15 shows a first segment 1500 of the original epoch 1300 from a seizure state, and FIG. 16 shows a second segment 1600 of the original epoch 1300 from a non-seizure state. FIG. 17 shows a first reconstructed sample 1700 of the first segment 1500, and FIG. 18 shows a second reconstructed sample 1800 of the second segment 1600. The total MSE of the reconstruction is $8.9 \times 10^{-4}$ and the absolute value of the averaged error per sample is $2.1 \times 10^{-2}$ for the original epoch 1300.

EXAMPLE 3

In this example, creating an implementation of the mother wavelet function from a second EEG signal and reconstructing the second EEG signal using a corresponding DWT is demonstrated. The second EEG signal recorded is from a 3-year-old male patient for approximately 50 hours using one model of channel montaging system and 25 separated recordings with 7 seizure events.

Figure 19:
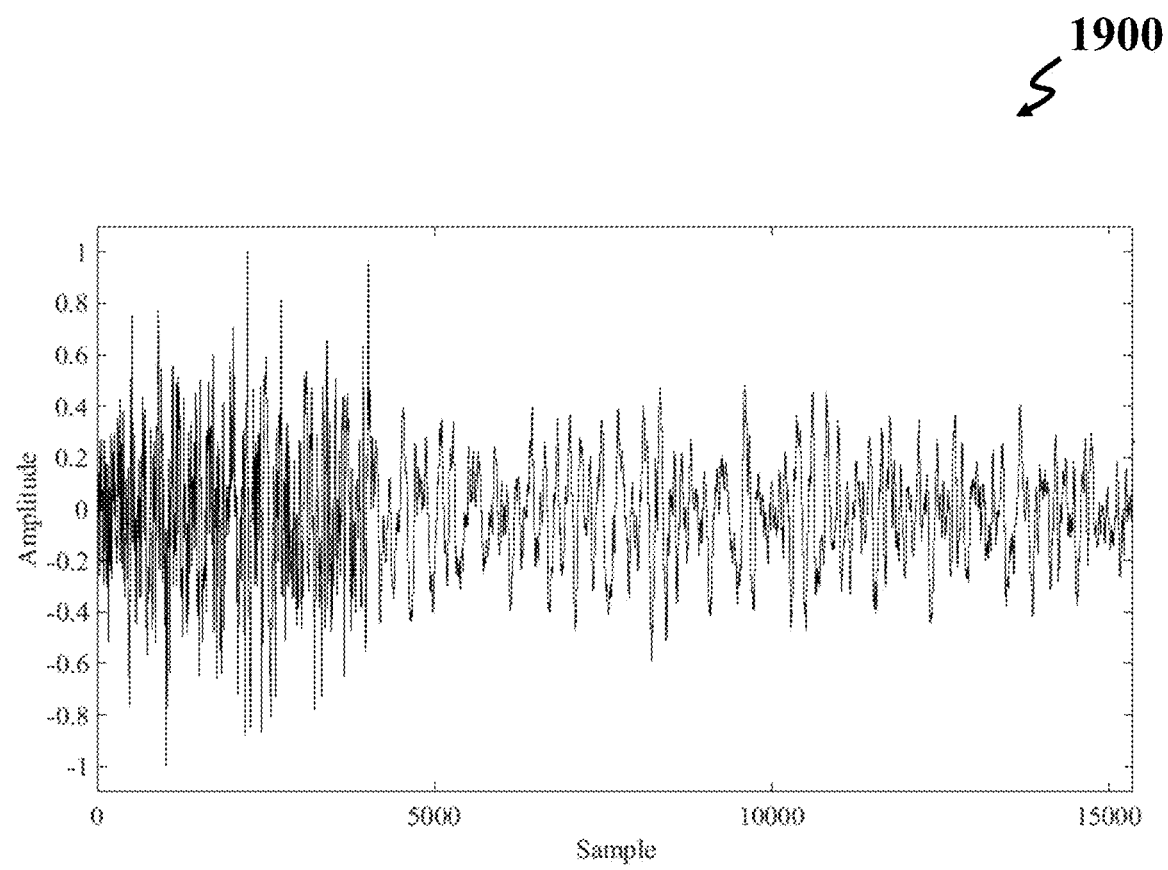
FIG. 19 shows an epoch obtained by windowing an EEG signal.

FIG. 19 shows an original epoch 1900 that is obtained by windowing the second EEG signal from a C3-P3 EEG channel for 60 seconds (i.e., 15360 samples based on a sampling frequency of 256 Hz and a 16-bit resolution). The original epoch 1900 is selected so that the non-seizure, seizure and also an offset event (a seizure to a non-seizure transition state) are observable in the original epoch 1900.

Figure 20:
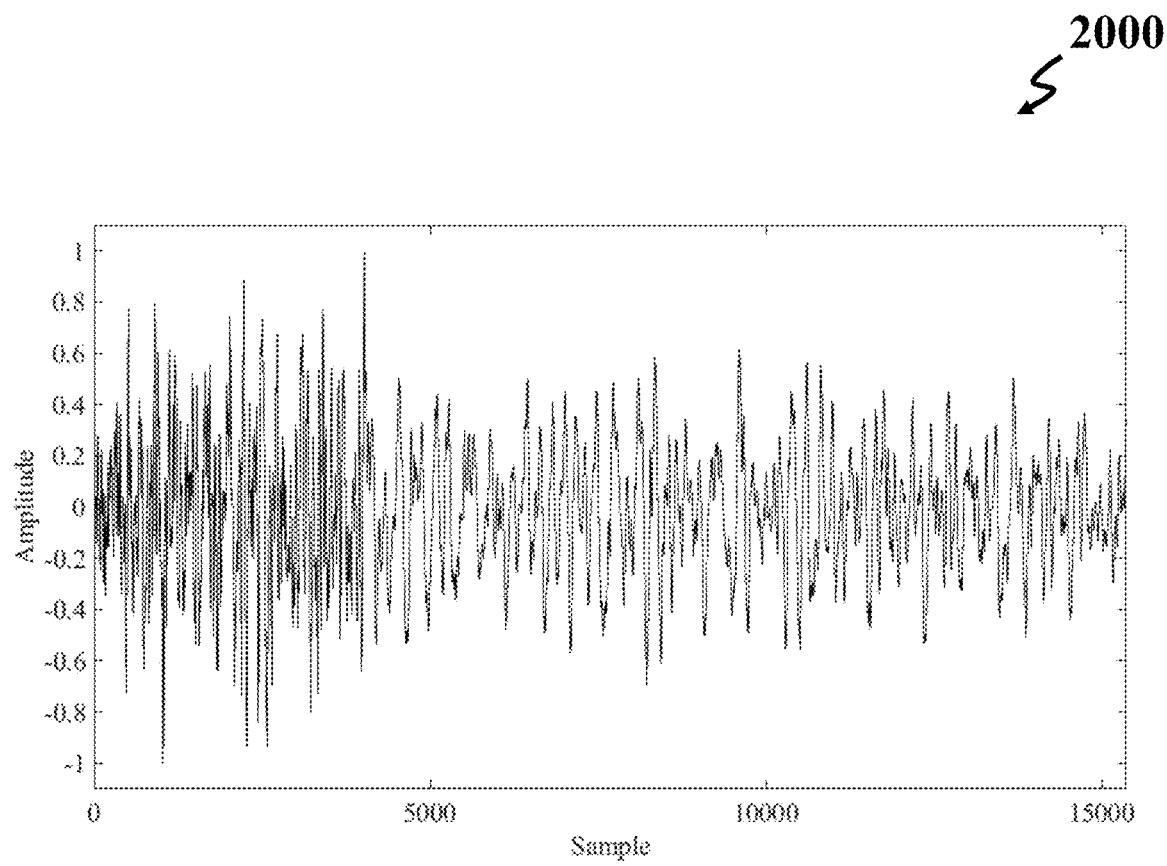
FIG. 20 shows a reconstructed epoch obtained by applying a DWT on an original epoch and perfect reconstructing the original epoch by an inverse DWT.
Figure 21:
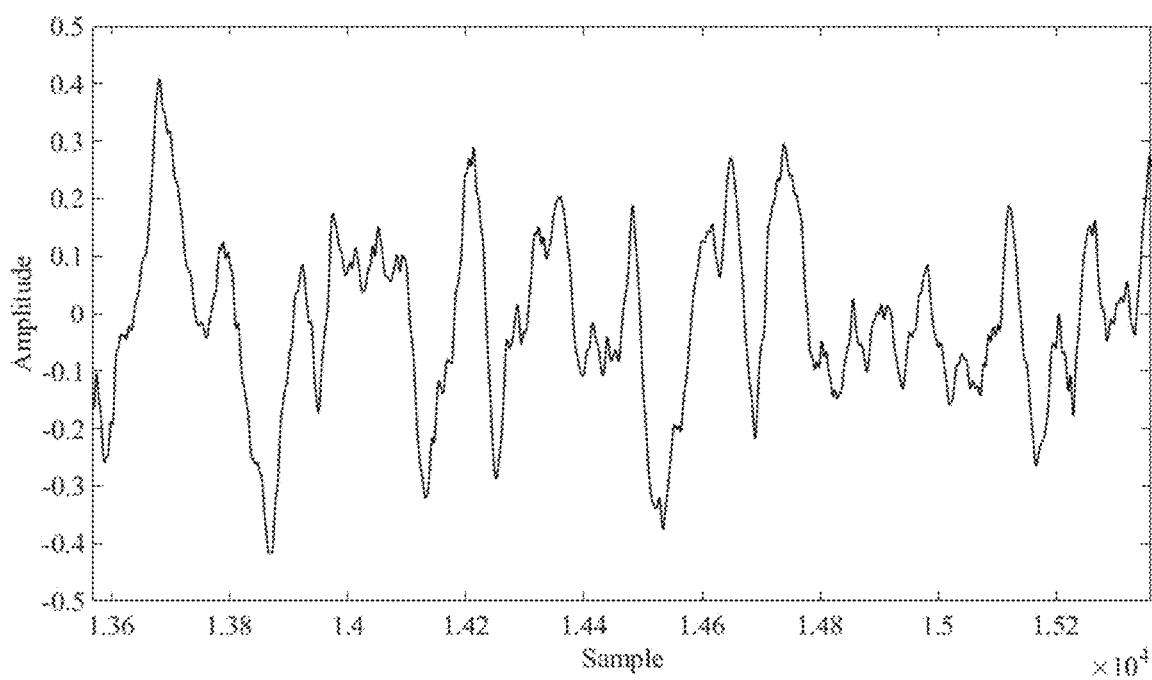
FIG. 21 shows a first segment of an original epoch from a non-seizure state.
Figure 22:
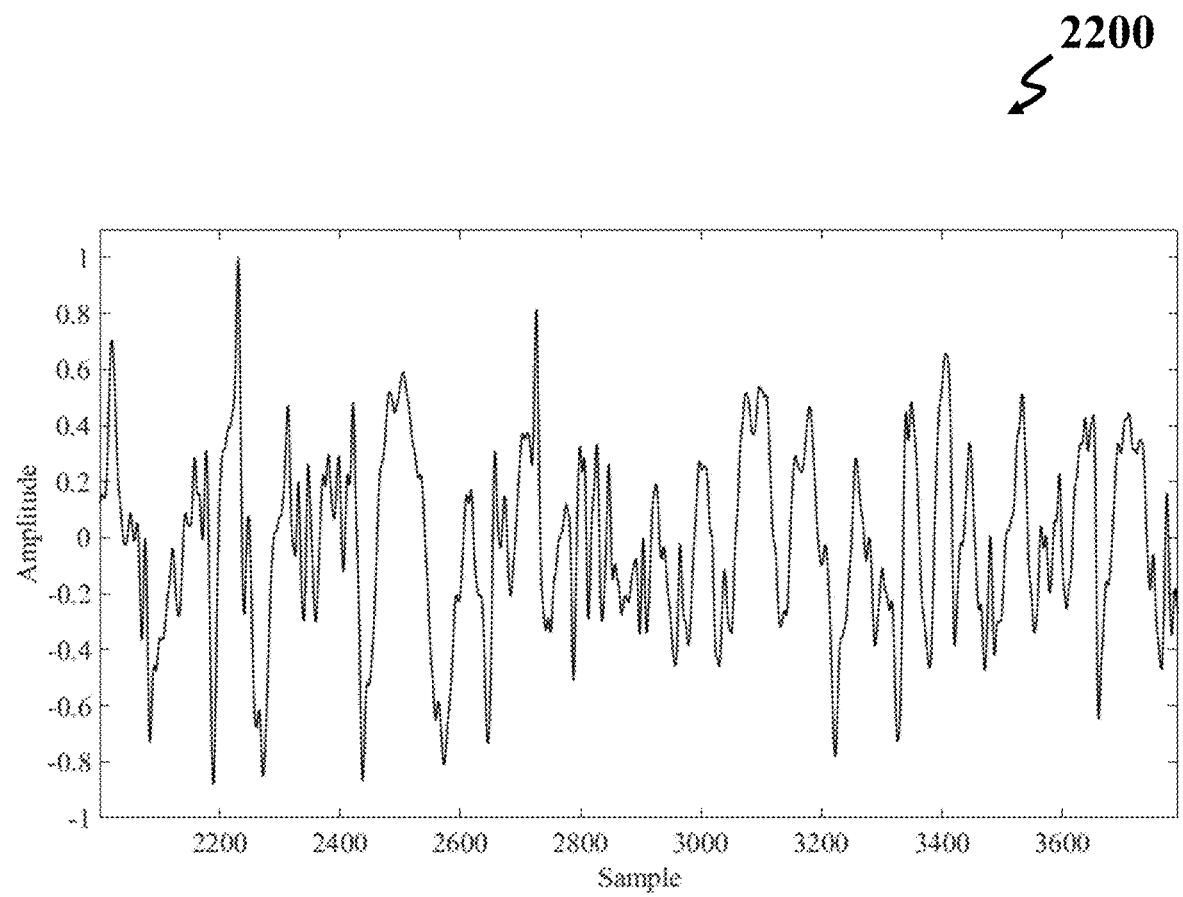
FIG. 22 shows a second segment of an original epoch from a seizure state.
Figure 23:
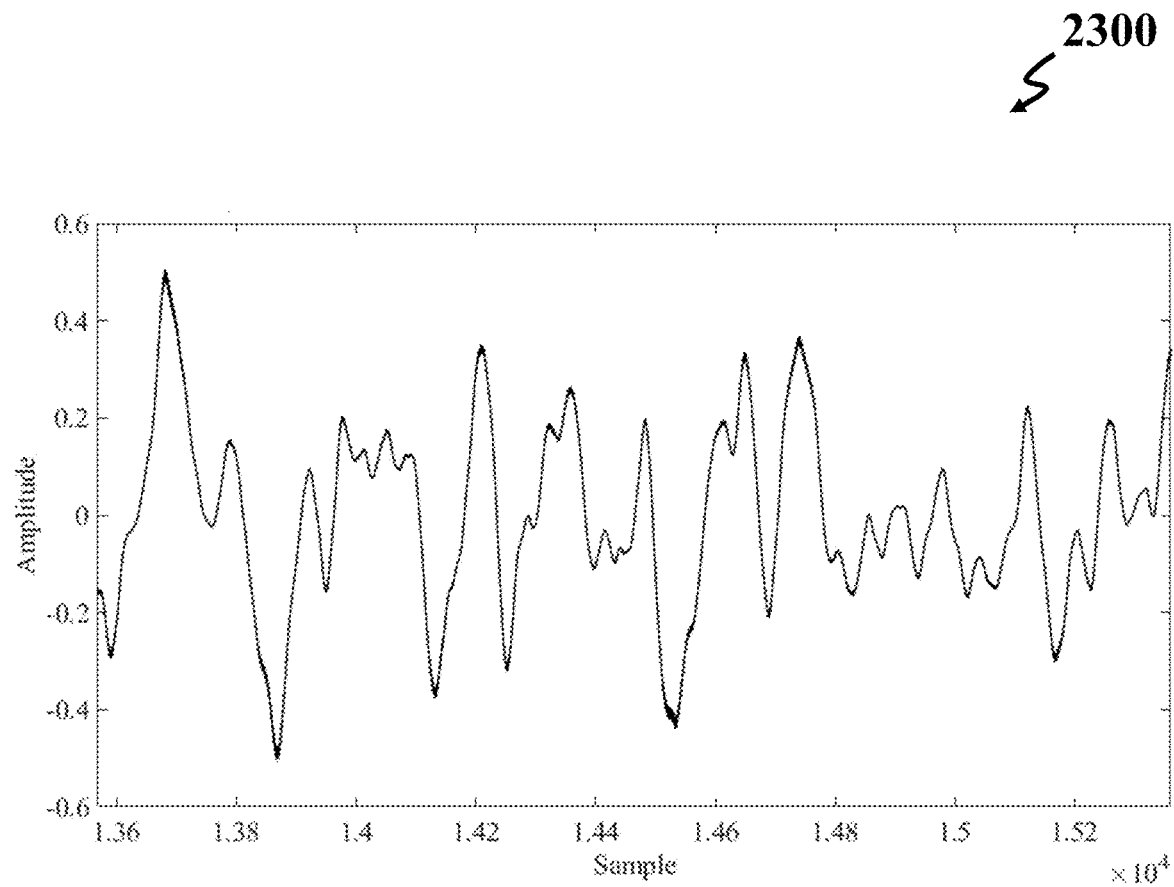
FIG. 23 shows a first reconstructed sample of a first segment of an original epoch.
Figure 24:
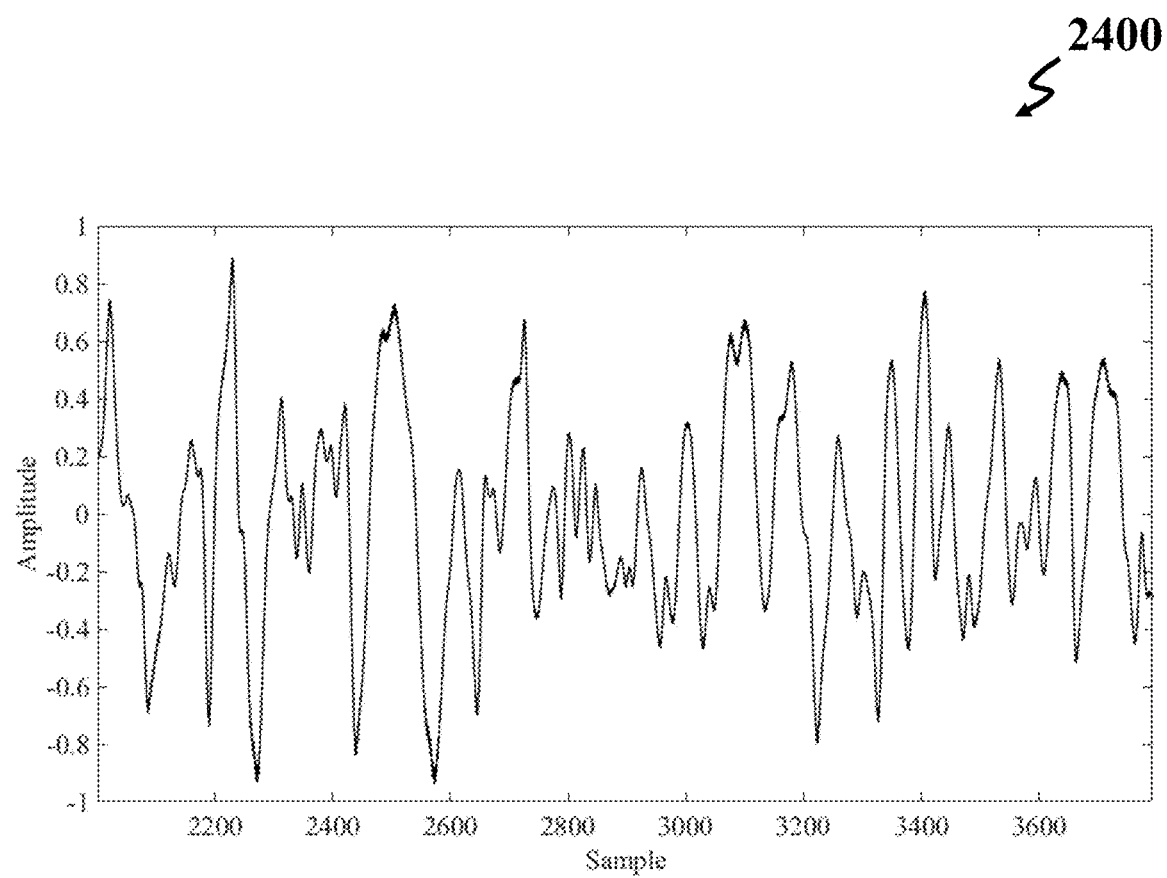
FIG. 24 shows a second reconstructed sample of a second segment of an original epoch.

FIG. 20 shows a reconstructed epoch 2000 that is obtained by applying the DWT in 1-level of decomposition and perfect reconstructing the original epoch 1900 by an inverse DWT. FIG. 21 shows a first segment 2100 of the original epoch 1900 from a non-seizure state, and FIG. 22 shows a second segment 2200 of the original epoch 1900 from a seizure state. FIG. 23 shows a first reconstructed sample 2300 of the first segment 2100, and FIG. 24 shows a second reconstructed sample 2400 of the second segment 2200. The total MSE of the reconstruction is $3.3 \times 10^{-3}$ and the absolute value of the averaged error per sample is $8.4 \times 10^{-3}$ for the original epoch 1900.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for creating a mother wavelet function for detecting epileptic seizure, the method comprising:
    placing a plurality of electroencephalography (EEG) electrodes on a scalp of a subject;
    acquiring, utilizing the plurality of EEG electrodes, a plurality of signals comprising a plurality of samples via a plurality of EEG channels associated with the plurality of EEG electrodes;
    extracting, utilizing one or more processors, a plurality of vectors from the plurality of EEG signals;
    extracting, utilizing the one or more processors, a kernel from the plurality of vectors by:
        estimating a multimodal ensemble probability density function (PDF) for a vector of the plurality of vectors; and
        choosing a sample of the vector with a maximum value in the multimodal ensemble PDF as a mode value of the vector;
    extracting, utilizing the one or more processors, the mother wavelet function from the kernel;
    extracting, utilizing the one or more processors, a plurality of features from the plurality of signals based on the mother wavelet function; and
    classifying, utilizing the one or more processors, each of the plurality of signals in one of a seizure class or a non-seizure class based on the plurality of features.

2. The method of claim 1, wherein extracting the plurality of vectors comprises:
    extracting a plurality of epochs from the plurality of signals, the plurality of epochs including a first epoch and a second epoch, each of the plurality of epochs including a given number of samples of the plurality of samples; and
    extracting the plurality of vectors from the plurality of epochs, each vector of the plurality of vectors including a first sample of the first epoch and a second sample of the second epoch.

3. The method of claim 2, wherein acquiring the plurality of signals comprises:
    band-pass filtering each of the plurality of signals based on a Kaiser-Bessel windowing procedure; and
    synchronizing the plurality of signals by an event-based approach.

4. The method of claim 1,
    further comprising updating the plurality of EEG channels based on a feedback from the one or more processors.

5. The method of claim 4, wherein estimating the multimodal PDF for the vector of the plurality of vectors includes using an expectation maximization (EM) technique for a Gaussian mixture model (GMM) of the vector.

6. The method of claim 1, wherein extracting the mother wavelet function includes:
    fitting a polynomial function to the kernel;
    generating a wavelet sealing function from the polynomial function; and
    generating the mother wavelet function from the sealing function.

7. The method of claim 6, wherein fitting the polynomial function to the kernel includes:
    generating a resampled kernel by resampling the kernel with a given resampling rate;
    generating a local maximum array including a plurality of local maximum values of the resampled kernel; and
    fitting a Lagrange polynomial function to the local maximum array.

8. The method of claim 6, wherein generating the wavelet scaling function includes generating a function $\varphi(\gamma)$ according to an operation defined by $$\varphi(\gamma)=2^{j/2}p(2^j\gamma-k), \text{ where}$$

$\gamma$ is a variable;
p(•) is the polynomial function; and
j and k are integer parameters.

9. The method of claim 8, wherein generating the wavelet scaling function further includes normalizing the function $\varphi(\gamma)$ such that $\|\varphi(\gamma)\|=1$, where $\|\cdot\|$ is an $l_2$ norm operator.

10. The method of claim 6, wherein generating the mother wavelet function includes:
    generating a low-pass filter from the wavelet scaling function;
    generating a high-pass filter from the low-pass filters; and
    generating the mother wavelet function from the high-pass filter.

11. The method of claim 10, wherein generating the low-pass filter includes calculating an inverse discrete Fourier transform (IDFT) of a function $\hat{H}(\omega)$ satisfying a condition according to:

$$\hat{\varphi}(\omega) = \frac{1}{\sqrt{2}} \hat{H}\left(\omega^{\frac{1}{2}}\right)\hat{\phi}\left(\omega^{\frac{1}{2}}\right)$$

where $\omega$ is an angular frequency and $\hat{\varphi}(\omega)$ is a representation of the wavelet scaling function in a frequency domain which is obtained by calculating a discrete Fourier transform (DFT) of the wavelet scaling function.

12. The method of claim 10, wherein generating the high-pass filter includes calculating a function g(n) according to an operation defined by:

$$g(n) = (-1)^n h(N-1-n);$$

where n is a discrete time instant, N is an integer parameter, and h(•) is an N-point low-pass finite impulse response (FIR) filter.

13. The method of claim 10, wherein generating the mother wavelet function includes:

calculating a function according to an operation defined by:

$$\hat{\psi}(\omega) = \frac{1}{\sqrt{2}} \hat{G}\left(\omega^{\frac{1}{2}}\right) \hat{\varphi}\left(\omega^{\frac{1}{2}}\right), \text{ where:}$$

ω is an angular frequency, $\hat{G}(\omega)$ is a representation of the high-pass filter in a frequency domain which is obtained by calculating a discrete Fourier transform (DFT) of the high-pass filter, and $\hat{\varphi}(\omega)$ is a representation of the wavelet scaling function in a frequency domain which is obtained by calculating a discrete Fourier transform (DFT) of the wavelet scaling function; and calculating an inverse discrete Fourier transform (IDFT) of the function $\hat{\psi}(\omega)$.

14. A system for generating a mother wavelet function from a plurality of electroencephalography (EEG) signals for detecting epileptic seizure, the system comprising:

a plurality of EEG electrodes configured to acquire the plurality of EEG signals via a plurality of EEG channels, the plurality of EEG signals including a plurality of samples;

a memory having processor-readable instructions stored therein; and one or more processors configured to access the memory and execute the processor-readable instructions, which, when executed by the one or more processors configures the one or more processor to perform a method, the method comprising:

band-pass filtering each of the plurality of EEG signals based on a Kaiser-Bessel windowing procedure;

synchronizing the plurality of EEG signals by an event-based approach;

extracting a plurality of epochs from the plurality of EEG signals, the plurality of epochs including a first epoch and a second epoch, each of the plurality of epochs including a given number of samples of the plurality of samples;

extracting a plurality of vectors from the plurality of epochs, a vector of the plurality of vectors including a first sample of the first epoch and a second sample of the second epoch;

estimating a multimodal ensemble probability density function (PDF) for the vector by using an expectation maximization (EM) technique for a Gaussian mixture model (GMM) of the vector;

extracting a kernel from the plurality of vectors, the kernel including a mode value of the vector, mode value including a sample of the vector with a maximum value in the multimodal ensemble PDF;

generating a resampled kernel by resampling the kernel with a given resampling rate;

generating a local maximum array including a plurality of local maximum values of the resampled kernel;

fitting a Lagrange polynomial function to the local maximum array;

generating a low-pass filter from the wavelet scaling function;

generating a high-pass filter from the low-pass filter;

generating the mother wavelet function from the high-pass filter;

extracting a plurality of features from the plurality of EEG signals based on the mother wavelet functions; and classifying each of the plurality of EEG signals in one of a seizure class or a non-seizure class based on the plurality of features.

* * * * *